United States Patent
Lu et al.

(10) Patent No.: US 11,298,684 B2
(45) Date of Patent: Apr. 12, 2022

(54) CATALYST FOR OXIDATIVE COUPLING OF METHANE, PREPARATION METHOD THEREOF AND APPLICATION THEREOF

(71) Applicants: EAST CHINA NORMAL UNIVERSITY, Shanghai (CN); ZHEJIANG JIRUITONG NEW MATERIAL CO., LTD., Lishui (CN)

(72) Inventors: Yong Lu, Shanghai (CN); Xin Zhang, Shanghai (CN); Pengwei Wang, Shanghai (CN); Guofeng Zhao, Shanghai (CN); Ye Liu, Shanghai (CN); Mingyuan He, Shanghai (CN)

(73) Assignees: EAST CHINA NORMAL UNIVERSITY, Shanghai (CN); ZHEJIANG JIRUITONG NEW MATERIAL CO., LTD., Lishui (CN)

( * ) Notice: Subject to any disclaimer, the term of this patent is extended or adjusted under 35 U.S.C. 154(b) by 0 days.

(21) Appl. No.: 16/494,173

(22) PCT Filed: Mar. 12, 2018

(86) PCT No.: PCT/CN2018/078709
§ 371 (c)(1),
(2) Date: Sep. 13, 2019

(87) PCT Pub. No.: WO2018/166419
PCT Pub. Date: Sep. 20, 2018

(65) Prior Publication Data
US 2020/0009534 A1    Jan. 9, 2020

(30) Foreign Application Priority Data
Mar. 13, 2017 (CN) .......................... 201710146190.1

(51) Int. Cl.
*B01J 23/34*  (2006.01)
*B01J 23/00*  (2006.01)
(Continued)

(52) U.S. Cl.
CPC .............. *B01J 23/34* (2013.01); *B01J 23/002* (2013.01); *B01J 23/30* (2013.01); *B01J 35/1014* (2013.01);
(Continued)

(58) Field of Classification Search
CPC ............ B01J 23/34; B01J 23/00; B01J 23/30; B01J 35/10; B01J 37/34; B01J 23/002;
(Continued)

(56) References Cited

U.S. PATENT DOCUMENTS

2006/0285993 A1* 12/2006 Rakowski ............. H01M 8/021
                                                              420/70
2008/0262114 A1   10/2008 Reynhout
(Continued)

FOREIGN PATENT DOCUMENTS

CN    1389293 A    1/2003
CN    1187118 C    2/2005
(Continued)

OTHER PUBLICATIONS

WO-2015101345-A1_English Translation (Year: 2015).*
(Continued)

*Primary Examiner* — Brian A McCaig
(74) *Attorney, Agent, or Firm* — Volpe Koenig

(57) ABSTRACT

A catalyst for oxidative coupling of methane, and preparation and application thereof. The catalyst comprises: a manganese sesquioxide, a tungstate, a manganese composite oxide having a perovskite structure and/or a spinel structure, and a carrier. The manganese sesquioxide, tungstate, and manganese composite oxide having a perovskite structure
(Continued)

and/or a spinel structure are supported on the carrier, or the manganese sesquioxide and tungstate are supported on the admixture of the said manganese composite oxide having a perovskite structure and/or a spinel structure and the said carrier. Based on 100 parts by weight of the catalyst, the content of the manganese sesquioxide is a parts by weight, the content of the tungstate is b parts by weight, the content of the manganese composite oxide having the perovskite structure and/or the spinel structure is c parts by weight The content of the carrier is d parts by weight. $0<a\leq 20$, $1\leq b\leq 20$, $1\leq c\leq 40$, $20\leq d<98$.

10 Claims, 3 Drawing Sheets

(51) Int. Cl.
| | |
|---|---|
| *B01J 23/30* | (2006.01) |
| *B01J 35/10* | (2006.01) |
| *B01J 37/04* | (2006.01) |
| *B01J 37/08* | (2006.01) |
| *B01J 37/34* | (2006.01) |
| *C07C 2/84* | (2006.01) |

(52) U.S. Cl.
CPC ....... *B01J 35/1019* (2013.01); *B01J 35/1023* (2013.01); *B01J 35/1071* (2013.01); *B01J 35/1076* (2013.01); *B01J 37/04* (2013.01); *B01J 37/08* (2013.01); *B01J 37/343* (2013.01); *C07C 2/84* (2013.01)

(58) Field of Classification Search
CPC .. B01J 23/005; B01J 23/8892; B01J 35/0006; B01J 35/002; B01J 35/1014; B01J 35/1019; B01J 35/1023; B01J 35/1042; B01J 35/1061; B01J 35/1071; B01J 35/1076; B01J 37/0036; B01J 37/0205; B01J 37/04; B01J 37/08; B01J 37/088; B01J 37/343; B01J 2523/00; B01J 2523/24; B01J 2523/3706; B01J 2523/72; B01J 2523/842; C07C 2/82; C07C 2/84; C07C 2523/30; C07C 2523/34; C07C 2523/889; Y02P 20/52
See application file for complete search history.

(56) References Cited

U.S. PATENT DOCUMENTS

| | | | |
|---|---|---|---|
| 2008/0281136 A1* | 11/2008 | Bagherzadeh | ......... B01J 23/002 585/310 |
| 2013/0178680 A1 | 7/2013 | Ha et al. | |
| 2020/0009534 A1 | 1/2020 | Lu et al. | |

FOREIGN PATENT DOCUMENTS

| | | | |
|---|---|---|---|
| CN | 104759291 A | 7/2015 | |
| CN | 105170138 A | 12/2015 | |
| CN | 106964341 A | 7/2017 | |
| CN | 104759291 B | 1/2018 | |
| CN | 106964341 B | 6/2019 | |
| JP | 2007254305 A | 3/2007 | |
| JP | 2007254305 A | 10/2007 | |
| WO | 2008087147 A1 | 7/2008 | |
| WO | 2015101345 A1 | 7/2015 | |
| WO | WO-2015101345 A1 * | 7/2015 | .............. B01J 23/34 |

OTHER PUBLICATIONS

Jaromin, A.L. (2004) Phase Stability of Beta-Gallia Rutile Intergrowths, Masters Thesis, Alfred University, 65pp.*
Yang, D. "New Progress in Preparation of Ethylene by Methane" (1985) [J] Liaoning Chemical Industry 01: 10-15. English Abstract Provided.
Wang, P. et al. "MnTiO3-Driven Low-Temperature Oxidative Coupling of Methane over TiO2-Doped Mn2O3—Na2WO4/SiO2 Catalyst" (2017) Sci Adv. 3(6): 1-9.
Wang, P. et al. "MnTiO3-Driven Low-Temperature Oxidative Coupling of Methane over TiO2-Doped Mn2O3—Na2WO4/SiO2 Catalyst" (2017) Sci. Adv. 3(6): e1603180 (1-9).
Wang, P.W. et al. "MnTiO3-Driven Low-Temperature Oxidative Coupling of Methane Over TiO2-doped Mn2O3—Na2WO4/SiO2 catalyst" (2017) Sci. Adv. 3(6).
Brusentsov Yu.A. and Minaev A.M., Fundamentals of physics and technology of oxide semiconductors: Textbook, Tambov, Publishing house of TSTU, 2002, sections 1 and 7.

* cited by examiner

CATALYST FOR OXIDATIVE COUPLING OF METHANE, PREPARATION METHOD THEREOF AND APPLICATION THEREOF

CROSS REFERENCE

This application is a 35 USC § 371 national stage of PCT/CN2018/078709, which was filed Mar. 13, 2018 and claims priority to Chinese Application No. 201710146190.1, which was filed on Mar. 13, 2017 and is entitled "Catalyst for low-temperature oxidative coupling of methane and preparation method and application of such catalyst," both of which are incorporated herein by reference as if fully set forth.

FIELD

The present disclosure relates to the technical field of catalysts and, more specifically, to preparation methods of the catalysts and applications of the catalysts, and to methods for oxidative coupling of methane.

BACKGROUND

Methane and olefins (such as ethylene) are important chemical raw materials. To date, several types of process for direct conversion from methane to olefins have been established, such as the Benson process, partial oxidation process, and catalytic pyrolysis process (Liaoning Chemical Industry, 1985, 1, 11). Due to the existence of by-product chlorinated hydrocarbons in the traditional Benson method, it has certain difficulties for separation. And the catalytic pyrolysis method produces a large amount of carbon deposit, which seriously affects the stability and working life of the catalyst. Hence, the partial oxidation process has currently become the main research direction of the preparation of olefins, among which oxidative coupling of methane, as one of the most promising of the above approaches to date, tantalizes enthusiasm from catalytic scientists all over the world in the past ten years.

Up to date, the catalysts for oxidative coupling of methane reaction are mainly grouped in three categories: alkaline and alkaline-earth metal oxide catalysts, rare-earth metal oxide catalysts, and transition metal composite oxide catalysts. These catalyst systems were almost all established in the 90s of 20th century. The problem is that product selectivity is low (generally no higher than 70%) at a relatively high methane conversions (>25%), making it difficult to meet economic requirements. In addition, the high reaction temperature (>800° C.) is extremely demanding on the material of the reactor, etc., greatly reducing the economics of the production process. For oxidative coupling of methane catalyst development, hence, the design of specific functions of catalytic materials that achieve high activity and selectivity at low temperature (<700° C.), is currently a challenging and difficult topic.

Chinese Application No. CN02119567.6 discloses a $SiO_2$ supported $Mn_2O_3$, $Na_2WO_4$ and $SnO_2$ catalyst. Such catalyst is capable of converting 33% methane with a $C_2^+$ yield of 24% at >700° C. and 0.6 MPa. However, fire and explosion hazards are the potential safety issues for oxidative coupling of methane process operated with pressure at >700° C., which greatly restricts its industrial application development.

Chinese Application No. CN201410001437.7 describes a manganese-sodium-tungsten-silicon composite oxide oxidative coupling of methane catalyst containing or not containing titanium, obtained by loading manganese nitrate (or one manganese precursor selected from manganese chloride, manganese acetate and manganese sulphate), sodium tungstate and ammonium tungstate onto a titanosilicate zeolite or a pure silica zeolite by means of a step-by-step impregnation method and subsequent calcination. The manganese-sodium-tungsten-silicon composite oxide catalyst containing or not containing titanium has the following structural formula: $vMnO_2 \cdot xNa_2O \cdot yWO_3 \cdot zTiO_2 \cdot (100-v-x-y-z)SiO_2$. The manganese-sodium-tungsten-silicon composite oxide catalysts containing or not containing titanium set forth in the application shows XRD patterns similar with their corresponding titanosilicate zeolite or pure silica zeolite carriers while no any phase diffraction peaks related to active components were observed, indicating the high dispersion of these active components on the zeolite carriers. Such catalysts are capable of converting more than 25% methane with high $C_2$-$C_3$ yield of 72-81% at 750-800° C. and atmospheric pressure in a wide range of gas hourly space velocity (10000~35000 mL·g$^{-1}$·h$^{-1}$). However, these catalysts become almost inactive when the reaction temperature is below 700° C. Only on the condition that the reaction temperature is relatively high, higher than 700° C., for example 750-800° C., can the catalysts exhibit better activity and selectivity. In such circumstance, it still cannot meet the requirements of low-temperature industrial production.

SUMMARY

In view of the above problems and needs existing in the prior art, the present disclosure aims at providing a catalyst and a method of making the same, application thereof, as well as a method for the oxidative coupling of methane.

In order to achieve the above object, a first aspect of the present disclosure provides a methane oxidative coupling catalyst consisting of three active components of manganese sesquioxide, sodium tungstate, and manganese titanium trioxide, and a carrier of silica. The catalyst has the following structural formula: $xMn_2O_3$-$yNa_2WO_4$-$zMnTiO_3$-$(100-x-y-z)SiO_2$, wherein x, y and z respectively representing the weight fraction occupied by manganese sesquioxide, sodium tungstate, manganese titanate in the catalyst, and wherein $0<x\leq20$, $1\leq y\leq20$, $1\leq z\leq40$.

As a preferred solution, in the $xMn_2O_3$-$yNa_2WO_4$-$zMnTiO_3$-$(100-x-y-z)SiO_2$ catalyst, the weight fraction occupied by the manganese sesquioxide, sodium tungstate, manganese titanate is each further in the range of $1.5\leq x\leq18$, $4\leq y\leq18$, and $2\leq z\leq35$.

A second aspect of the present disclosure provides a preparation method of the catalyst for oxidative coupling of methane, comprising:

a) grinding $MnTiO_3$ and $SiO_2$ thoroughly to form a uniform powder admixture;

b) at room temperature, dropwise adding the aqueous solution of $Na_2WO_4$ to the admixture of $MnTiO_3$ and $SiO_2$ obtained in step a); and then ultrasonically dispersing for 0.5-1 hour and subsequently mechanically stirring for 1-3 hours to obtain a slurry thick paste;

c) dropwise adding the aqueous solution of $Mn(NO_3)_2$ to the slurry thick paste obtained in step b) under stirring at room temperature; stirring was continued for 1-3 hours; and then dried at 80-100° C.;

d) grinding the dried product obtained in step c) into a powder; calcining the ground powder in an air atmosphere at 500-900° C. for 1-2 hours.

A third aspect of the present disclosure provides another preparation method of the catalyst for oxidative coupling of methane, comprising:

A) at room temperature, dropwise adding the aqueous solution of $Na_2WO_4$ to $SiO_2$; ultrasonically dispersing for 0.5-1 hour and subsequently mechanically stirring for 1-3 hours to obtain a slurry thick paste;

B) dropwise adding the aqueous solution of $Mn(NO_3)_2$ to the slurry thick paste obtained in step A) under stirring at room temperature; stirring was continued the admixture for 1-3 hours; and then dried at 80° C.-100° C.;

C) grinding the dried product obtained in step B) with $MnTiO_3$ into a homogeneous powder; calcining the ground homogeneous powder in an air atmosphere at 500-900° C. for 1-2 hours.

A forth aspect of the present disclosure provides a catalyst, comprising a manganese sesquioxide, a tungstate, a manganese composite oxide having a perovskite structure and/or a spinel structure, and a carrier, wherein the manganese sesquioxide, the tungstate, the manganese composite oxide having a perovskite structure and/or a spinel structure are supported on the carrier, or the manganese sesquioxide and the tungstate are supported on the admixture of the said manganese composite oxide having a perovskite structure and/or a spinel structure and the said carrier. In the catalyst, based on 100 parts by weight of the catalyst, the content of the manganese sesquioxide is a parts by weight, the content of the tungstate is b parts by weight, the content of the manganese composite oxide having the perovskite structure and/or the spinel structure is c parts by weight, and the content of the carrier is d parts by weight, and wherein $0<a\leq20$, $1\leq b\leq20$, $1\leq c\leq40$, $20\leq d<98$.

A fifth aspect of the present disclosure provides a preparation method of a catalyst, comprising:

1) admixing the manganese composite oxide having the perovskite structure and/or the spinel structure with the carrier in solid-phase to obtain a solid phase admixture A;

2) admixing a precursor of tungstate salt and a precursor of manganese sesquioxide with the solid phase admixture A obtained in step 1) to obtain an admixture B;

3) subsequently drying and calcining the admixture B obtained in step 2).

A sixth aspect of the present disclosure provides another preparation method of the catalyst, comprising:

i) admixing a precursor of tungstate salt and a precursor of manganese sesquioxide with the carrier in the presence of a solvent to obtain a mixed product X;

ii) drying the mixed product X obtained in step i) to obtain a dried product Y;

iii) admixing the manganese composite oxide having the perovskite structure and/or the spinel structure with the dried product Y obtained in step ii) in solid-phase and then calcining.

A seventh aspect of the present disclosure provides the catalysts obtained by above described methods.

An eighth aspect of the present disclosure provides an application of the above described catalysts or the catalysts obtained by the above described method in oxidative coupling of methane.

A ninth aspect of the present disclosure provides a method for oxidative coupling of methane, comprising: bringing a catalyst into contact with a feed gas stream containing methane and oxygen to have the methane reacting with oxygen under oxidative coupling of methane conditions, wherein the catalyst is the each one chosen from the above described catalysts or the catalysts obtained by the above described preparation method.

As indicated by experimental results, the catalysts provided by the present disclosure or the catalysts obtained by the preparation method provided by the present disclosure, achieve unprecedented low-temperature activity and selectivity for oxidative coupling of methane, due to the presence of the manganese composite oxide having a perovskite structure and/or a spinel structure. Such catalysts are capable of converting 27% methane with a high $C_2$-$C_3$ hydrocarbon selectivity of 76% even at low reaction temperature of 620-700° C., achieving the results that the prior art can only be realized at a temperature higher than 750° C., and therefore making oxidative coupling of methane reaction process more beneficial to commercialization. More specially, in the prior art, the catalysts become almost inactive at or below 700° C. and it is even more impossible to talk about selectivity. Compared with the prior art, thus, the present disclosure has also made remarkable progress.

DETAILED DESCRIPTION

Figure 1:
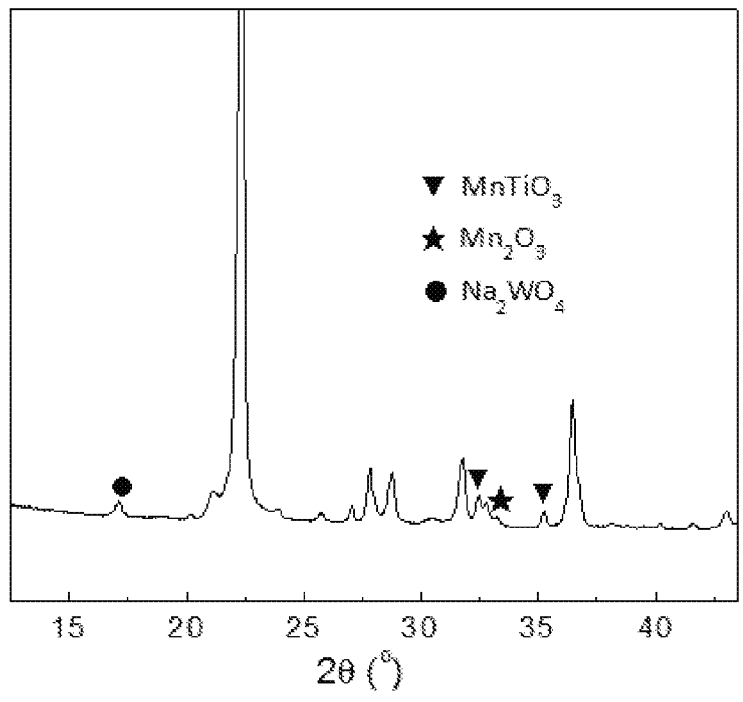
FIG. 1 is the X-ray diffraction pattern of $3Mn_2O_3$-$10Na_2WO_4$-$10MnTiO_3$-$77SiO_2$ catalyst as prepared in Example 1.

In the present disclosure, the endpoints and any values of the ranges disclosed herein are not limited to the precise ranges or values, and these ranges or values should be understood to include values close to these ranges or values. For numerical ranges, the endpoint values of the various ranges, the endpoint values of the various ranges and the individual point values, and individual point values can be combined with one another to obtain one or more new numerical ranges, these numerical ranges should be considered as specifically disclosed herein.

As mentioned above, a first aspect of the present disclosure provides a methane oxidative coupling catalyst consisting of three active components of manganese sesquioxide, sodium tungstate, and manganese titanium trioxide, and a carrier of silica. The catalyst has the following structural formula: $xMn_2O_3\text{-}yNa_2WO_4\text{-}zMnTiO_3\text{-}(100\text{-}x\text{-}y\text{-}z)SiO_2$, wherein x, y and z respectively representing the weight fraction occupied by manganese sesquioxide, sodium tungstate, manganese titanate in the catalyst, and wherein $0<x\leq20$, $1\leq y\leq20$, $1\leq z\leq40$.

According to the present disclosure, in as-described catalyst structural formula, the connection symbols between the components have no special meaning and there is no special requirement for the arrangement sequence of the components; the as-described catalyst structural formula only represents that the catalyst contains the following components, the x, y, z and (100-x-y-z) respectively representing the weight fraction occupied by manganese sesquioxide ($Mn_2O_3$), sodium tungstate ($Na_2WO_4$), manganese titanate ($MnTiO_3$), and silica ($SiO_2$).

According to the present disclosure, Ti is selected as a modified element in a targeted way, which can be transformed into $TiO_2$ auxiliary agent during oxidative coupling of methane reaction and modify the $SiO_2$ carrier supported components $Mn_2O_3$ and $Na_2WO_4$. The $MnTiO_3$ is generated from $TiO_2$ auxiliary agent and $Mn_2O_3$ at low temperature, which can effectively reduce the temperature for $O_2$ activation in oxidative coupling of methane and triggers the low-temperature chemical cycle for $O_2$ activation to drive the low-temperature oxidative coupling of methane thereby leading to a significant reduction of the reaction temperature from 800-900° C. for the prior art to less than 700° C. The essence of this effect lies in the formation of low temperature chemical cycle "$MnTiO_3 \leftrightarrow Mn_2O_3$", that is, the introduced $TiO_2$ acts as a low-temperature active "catalyst" to catalyze the reduction-oxidation reaction of $Mn_2O_3$ with methane ($CH_4$) in association with the formation of $MnTiO_3$ at a low temperature, and meanwhile, the as-formed $MnTiO_3$ can react with oxygen at a relatively low temperature to form $Mn_2O_3$ and $TiO_2$. At the same time, the low temperature chemical cycle works synergistically with $Na_2WO_4$ to achieve high selectivity regulation of the target product.

According to the present disclosure, in order to effectively exert the synergistic effect of the components for obtaining a methane oxidative coupling catalyst with low temperature, high activity and high selectivity, the weight fraction occupied by the manganese sesquioxide, sodium tungstate, and manganese titanate is in range of $0<x\leq20$, $1\leq y\leq20$, and $1\leq z\leq40$, respectively, and preferably is $1.5\leq x\leq18$, $4\leq y\leq18$, and $2\leq z\leq35$, respectively.

A second aspect of the present disclosure provides a preparation method of the catalyst for oxidative coupling of methane, comprising:

a) grinding $MnTiO_3$ and $SiO_2$ thoroughly to form a uniform powder admixture;

b) at room temperature, dropwise adding the aqueous solution of $Na_2WO_4$ to the admixture of $MnTiO_3$ and $SiO_2$ obtained in step a); and then ultrasonically dispersing for 0.5-1 hour and subsequently mechanically stirring for 1-3 hours to obtain a slurry thick paste;

c) dropwise adding the aqueous solution of $Mn(NO_3)_2$ to the slurry thick paste obtained in step b) under stirring at room temperature; stirring was continued for 1-3 hours; and then dried at 80° C.-100° C.;

d) grinding the dried product obtained in step c) into a powder; calcining the ground powder in an air atmosphere at 500-900° C. for 1-2 hours.

A third aspect of the present disclosure provides another preparation method of the catalyst for oxidative coupling of methane, comprising:

A) at room temperature, dropwise adding the aqueous solution of $Na_2WO_4$ to $SiO_2$; ultrasonically dispersing for 0.5-1 hour and subsequently mechanically stirring for 1-3 hours to obtain a slurry thick paste;

B) dropwise adding the aqueous solution of $Mn(NO_3)_2$ to the slurry thick paste obtained in step A) under stirring at room temperature; stirring was continued the admixture for 1-3 hours; and then dried at 80° C.-100° C.;

C) grinding the dried product obtained in step B) with $MnTiO_3$ into a homogeneous powder; calcining the ground homogeneous powder in an air atmosphere at 500-900° C. for 1-2 hours.

A forth aspect of the present disclosure provides a catalyst, comprising a manganese sesquioxide, a tungstate, a manganese composite oxide having a perovskite structure and/or a spinel structure, and a carrier, wherein the manganese sesquioxide, the tungstate, the manganese composite oxide having a perovskite structure and/or a spinel structure are supported on the carrier, or the manganese sesquioxide and the tungstate are supported on the admixture of the said manganese composite oxide having a perovskite structure and/or a spinel structure and the said carrier, wherein since the manganese composite oxide having a perovskite structure and/or a spinel structure is a relatively large particle, it is generally considered that the perovskite structure and/or the spinel structure of the manganese composite oxide is not present in the form of loading on the carrier, but coexists in the form of a mixture.

Preferably, in the catalyst, based on 100 parts by weight of the catalyst, the content of the manganese sesquioxide is a parts by weight, the content of the tungstate is b parts by weight, the content of the manganese composite oxide having the perovskite structure and/or the spinel structure is c parts by weight, and the content of the carrier is d parts by weight, wherein $0<a\leq20$, preferably $1.5\leq a\leq18$, $1\leq b\leq20$, preferably $4\leq b\leq18$, $1\leq c\leq40$, preferably $2\leq c\leq35$, $20\leq d\leq98$, preferably $29\leq d\leq92.5$.

According to the present disclosure, oxides which can interact with manganese oxide to form manganese composite oxides having perovskite structures and/or spinel structures at low temperature are selected in a targeted way to use as modifiers to modify the supported catalyst systems containing manganese sesquioxide and tungstate. By doing so, the catalyst described in the present disclosure can form a chemical cycle between "manganese sesquioxide" and "manganese composite oxides having perovskite structures and/or spinel structures" in the low-temperature methane oxidative coupling reaction process, that is, the oxides of specific doping elements introduced show the ability to catalyze the reduction-oxidation reaction of $Mn_2O_3$ with methane in association with the formation of the manganese composite oxides having perovskite structures and/or the spinel structures, and meanwhile, as-formed manganese composite oxides having perovskite structures and/or spinel structures can react with oxygen at a relatively low temperature to form $Mn_2O_3$ and the oxides of specific doping elements introduced. In the traditional supported catalyst system containing manganese sesquioxide and tungstate, the chemical cycle works in the way of "$MnWO_4 \leftrightarrow Mn_2O_3$", which proceeds only at high reaction temperature. Therefore, the reason why the catalyst described in the present disclosure can form a chemical cycle between "manganese sesquioxide" and "manganese composite oxides having perovskite structures and/or spinel structures" in the low-temperature methane oxidative coupling reaction process is precisely because the formation of manganese composite oxides having perovskite structures and/or spinel structures replaces the formation of $MnWO_4$. Specially, the chemical cycle between "manganese sesquioxide" and "manganese composite oxides having perovskite structures and/or spinel structures" works synergistically with $Na_2WO_4$ to selectively convert methane into $C_2$-$C_3$. Moreover, the present disclosure provides a new idea for direct activation and conversion of methane, the catalyst modification described in the present disclosure leads to a significant reduction of reaction temperature of oxidative coupling of methane while achieving high methane conversion and $C_{2+}$ selectivity. Furthermore, the catalyst provided in the present disclosure, comprising a manganese sesquioxide, a tungstate, a manganese composite oxide having a perovskite structure and/or a spinel structure, and a carrier, shows good stability, showing excellent maintenance of high methane conversion and high $C_2$-$C_3$ selectivity during several hundred hours testing in oxidative coupling of methane at relatively high temperature.

According to the present disclosure, in order to more effectively exert the synergistic effect of the components for obtaining a methane oxidative coupling catalyst with lower temperature, higher activity and higher selectivity, it is necessary to further optimize the weight fraction occupied by the manganese sesquioxide, the tungstate, and the manganese composite oxide having a perovskite structure and/or a spinel structure, preferably, the catalyst is consisted of a manganese sesquioxide, a tungstate, a manganese composite oxide having a perovskite structure and/or a spinel structure, and a carrier.

In the catalyst, based on 100 parts by weight of the catalyst, the content of the manganese sesquioxide is ranged from >0 parts by weight to ≤20 parts by weight, for example, the content of the manganese sesquioxide can be 0.1 parts by weight, 0.2 parts by weight, 0.3 parts by weight, 0.4 parts by weight, 0.5 parts by weight, 1 parts by weight, 1.5 parts by weight, 2 parts by weight, 2.5 parts by weight, 3 parts by weight, 3.5 parts by weight, 4 parts by weight, 4.5 parts by weight, 5 parts by weight, 6 parts by weight, 7 parts by weight, 8 parts by weight, 9 parts by weight, 10 parts by weight, 11 parts by weight, 12 parts by weight, 13 parts by weight, 14 parts by weight, 15 parts by weight, 16 parts by weight, 17 parts by weight, 18 parts by weight, 19 parts by weight, 20 parts by weight, and any content between any two of the foregoing adjacent contents; the content of the tungstate is range from 1.0 parts by weight to 20 parts by weight, for example, the content of the tungstate can be 1 parts by weight, 1.5 parts by weight, 2 parts by weight, 2.5 parts by weight, 3 parts by weight, 3.5 parts by weight, 4 parts by weight, 4.5 parts by weight, 5 parts by weight, 6 parts by weight, 7 parts by weight, 8 parts by weight, 9 parts by weight, 10 parts by weight, 11 parts by weight, 12 parts by weight, 13 parts by weight, 14 parts by weight, 15 parts by weight, 16 parts by weight, 17 parts by weight, 18 parts by weight, 19 parts by weight, 20 parts by weight, and any content between any two of the foregoing adjacent contents; the content of the manganese composite oxide having a perovskite structure and/or a spinel structure is range from 1 parts by weight to 40 parts by weight, for example, the content of the manganese composite oxide having a perovskite structure and/or a spinel structure can be 1 parts by weight, 1.5 parts by weight, 2 parts by weight, 2.5 parts by weight, 3 parts by weight, 3.5 parts by weight, 4 parts by weight, 4.5 parts by weight, 5 parts by weight, 6 parts by weight, 7 parts by weight, 8 parts by weight, 9 parts by weight, 10 parts by weight, 11 parts by weight, 12 parts by weight, 13 parts by weight, 14 parts by weight, 15 parts by weight, 16 parts by weight, 17 parts by weight, 18 parts by weight, 19 parts by weight, 20 parts by weight, 21 parts by weight, 22 parts by weight, 23 parts by weight, 24 parts by weight, 25 parts by weight, 26 parts by weight, 27 parts by weight, 28 parts by weight, 29 parts by weight, 30 parts by weight, 31 parts by weight, 32 parts by weight, 33 parts by weight, 34 parts by weight, 35 parts by weight, 36 parts by weight, 37 parts by weight, 38 parts by weight, 39 parts by weight, 40 parts by weight, and any content between any two of the foregoing adjacent contents; the balance is the carrier.

Even more preferably, based on 100 parts by weight of the catalyst, the content of the manganese sesquioxide is ranged from 1.5 parts by weight to 18 parts by weight, the content of the tungstate is range from 4 parts by weight to 18 parts by weight, the content of the manganese composite oxide having a perovskite structure and/or a spinel structure is range from 2 parts by weight to 35 parts by weight, the balance is the carrier.

In the present disclosure, the phase composition of the catalyst is determined by means of X-ray powder diffraction method, the loading amount of each active component in the catalyst is measured by means of X-ray powder diffraction standard working curve method.

According to the present disclosure, in order to make the formation of the chemical cycle between "$Mn_2O_3$" and "manganese composite oxide having a perovskite structure and/or a spinel structure" become easier in oxidative coupling of methane process, preferably, the manganese composite oxide having a perovskite structure and/or a spinel structure comprises at least one element selected from Ti, Fe, Co, Ni, Li, Pb, Cd, Sn, In, Ge, Ga, Sb, Bi, Te, Se, Zr, Hf, V, Nb, Ta, Cr, Mo, W, Ba, Mg, Ce, La, Pr, Nd, Sm, Ca, Sr, Ba, K or combinations thereof.

According to the present disclosure, the manganese composite oxide having a perovskite structure and/or a spinel structure can be the manganese composite oxide having a perovskite structure and/or a manganese composite oxide having a double-perovskite structure. Specifically, when the manganese composite oxide has the perovskite structure, the manganese composite oxide comprises at least one selected from manganese titanate, manganese plumbate, manganese stannate, manganese indium trihydoxide, manganese germanate, manganese gallate, bismuth manganate, manganese tellurite, manganese selenate, vanadium manganate, manganese niobate, manganese tantalite, manganese chromate, barium manganate, magnesium manganate. When the manganese composite oxide has the double-perovskite structure, the manganese composite oxide comprises at least one selected from the group consisted of $LnAFeMnO_6$ (Ln is selected from La, Pr, Nd, Sm, Ce or combinations thereof; A is selected from Ca, Sr, Ba or combinations thereof), $La_{0.5}Sr_{0.5}Mn_{1-m}Fe_mO_3$, $Ca_\alpha La_\beta K_{1-\alpha-\beta}Mn_{0.5}Fe_{0.5}O_3$, $Ca_pLa_qK_{1-p-q}Mn_{0.78}Fe_{0.22}O_3$, $Bi_{0.5}Ca_{0.5-n}La_nFe_{0.3}Mn_{0.7}O_3$ or combinations thereof, wherein $0<m\leq0.25$, for example, m can be 0.05, 0.1, 0.12, 0.15, 0.2, 0.22, 0.24, 0.25, and any value between any two of the foregoing adjacent values, preferably $0.1\leq m\leq0.22$, $0<\alpha\leq0.25$, for example, α can be 0.05, 0.1, 0.12, 0.15, 0.2, 0.22, 0.24, 0.25, and any value between any two of the foregoing adjacent values; preferably $0.1\leq\alpha\leq0.2$, $0<\beta\leq0.25$, for example, β can be 0.05, 0.1, 0.12, 0.15, 0.2, 0.22, 0.24, 0.25, and any value between any two of the foregoing adjacent values; preferably $0.1\leq\beta\leq0.2$, $0<p\leq0.25$, for example, p can be 0.05, 0.1, 0.12, 0.15, 0.2, 0.22, 0.24, 0.25, and any value between any two of the foregoing adjacent values; preferably $0.1\leq p\leq0.2$, $0<q\leq0.25$, for example, q can be 0.05, 0.1, 0.12, 0.15, 0.2, 0.22, 0.24, 0.25, and any value between any two of the foregoing adjacent values; preferably $0.1\leq q\leq0.2$, $0<n\leq0.25$, for example, n can be 0.05, 0.1, 0.12, 0.15, 0.2, 0.22, 0.24, 0.25, and any value between any two of the foregoing adjacent values, preferably 0.1≤n≤0.2.

According to the present disclosure, the manganese composite oxide having the perovskite structure and/or the spinel structure can be the manganese composite oxide having the spinel structure as well. Specifically, the manganese composite oxide is at least one of manganese ferrite, manganese cobaltate, manganese nickelate, lithium manganate, manganese chromate, and lithium nickel cobalt manganese oxide.

According to the present disclosure, the carrier may be various inorganic heat-resistant oxides and/or carbide that do not adversely affect the catalyst, including but not limited to SiC, $Fe_2O_3$, $Fe_3O_4$, $TiO_2$, $ZrO_2$, $Al_2O_3$, $La_2O_3$, CaO, SrO, MgO, $SiO_2$ or combinations thereof. On the one hand, $SiO_2$ is economical; on the other hand, $SiO_2$ can be transformed into cristobalite phase that is beneficial to the catalytic activity of the catalyst. Hence, $SiO_2$ is preferably chosen as the carrier.

According to the present disclosure, preferably, the carrier comprises particles having the size varied from 100 to 2000 mash, even more preferably, from 100 to 1000 mesh; preferably, the carrier comprises particles having the specific surface varied from 10 to 1000 $m^2/g$, even more preferably, from 50 to 250 $m^2/g$; preferably, the carrier comprises particles having the pore volume varied from 0.1 to 1.2 mL/g, even more preferably, from 0.5 to 0.9 mL/g; preferably, the carrier comprises particles having the most probable pore size varied from 2.0 to 20 nm, even more preferably, from 2.0 to 10.0 nm. In this way, the carrier can be guaranteed to have higher specific surface area and provide more active sites thereby leading to improved catalytic performance of the catalyst. In the present disclosure, the specific surface and pore volume refer to BET specific surface and pore volume, and the most probable pore size is calculated from the adsorption curve using BJH (Barrett-Joyner-Halenda) model.

According to the present disclosure, the manganese composite oxide having the perovskite structure and/or the spinel structure comprises particles having size varied from 100 to 2000 mash, preferably, from 100 to 1000 mesh.

According to a preferred embodiment of the present disclosure, the manganese composite oxide having the perovskite structure and/or the spinel structure is manganese titanate ($MnTiO_3$), the catalyst is consisted of a manganese sesquioxide ($Mn_2O_3$), a sodium tungstate ($Na_2WO_4$), a manganese titanate ($MnTiO_3$), and a silica ($SiO_2$) carrier. When $MnTiO_3$ is chosen as the manganese composite oxide having the perovskite structure and/or the spinel structure, it means that Ti is selected as a modified element in a targeted way, which can be transformed into $TiO_2$ auxiliary agent during oxidative coupling of methane reaction and modify the $SiO_2$ carrier supported components $Mn_2O_3$ and $Na_2WO_4$. The $MnTiO_3$ is generated from $TiO_2$ auxiliary agent and $Mn_2O_3$ at low temperature, which can effectively reduce the temperature for $O_2$ activation in oxidative coupling of methane and and triggers the low-temperature chemical cycle for $O_2$ activation to drive the low-temperature oxidative coupling of methane thereby leading to a dramatic improvement of the low-temperature activity/selectivity associated with a significant reduction of the reaction temperature from 800-900° C. for the prior art to less than 700° C. The essence of this effect lies in the formation of low temperature chemical cycle "$MnTiO_3 \leftrightarrow Mn_2O_3$", that is, the introduced $TiO_2$ acts as a low-temperature active "catalyst" to catalyze the reduction-oxidation reaction of $Mn_2O_3$ with methane ($CH_4$) in association with the formation of $MnTiO_3$ at a low temperature, and meanwhile, the as-formed $MnTiO_3$ can react with oxygen at a relatively low temperature to form $Mn_2O_3$ and $TiO_2$. At the same time, the low temperature chemical cycle works synergistically with $Na_2WO_4$ to achieve high selectivity regulation of the target product.

As mentioned above, the fifth aspect of the present disclosure provides a preparation method of a catalyst, comprising: admixing a precursor of manganese sesquioxide, a precursor of tungstate salt, and a manganese composite oxide having a perovskite structure and/or a spinel structure with the carrier, and sequentially drying and calcining the admixture. To obtain the admixture comprising the manganese sesquioxide, the tungstate salt precursor, and the manganese composite oxide having the perovskite structure and/or the spinel structure, and the carrier, the admixing order can be: admixing the manganese composite oxide having the perovskite structure and/or the spinel structure with the carrier in solid-phase to obtain an admixture, successively admixing the precursor of tungstate salt and the precursor of manganese sesquioxide ($Mn_2O_3$) in the presence of a solvent with as-obtained admixture of last step, wherein the sequence of admixing the precursor of tungstate salt and the precursor of manganese sesquioxide ($Mn_2O_3$) in the presence of a solvent with as-obtained admixture of last step can be changed, the admixing order also can be: successively admixing the precursor of tungstate salt and the precursor of manganese sesquioxide ($Mn_2O_3$) with the carrier in the presence of a solvent to obtain a mixed product, drying the mixed product of last step and then admixing the manganese composite oxide having the perovskite structure and/or the spinel structure with the dried mixed product of last step in solid-phase, wherein the sequence of admixing the precursor of tungstate salt and the precursor of manganese sesquioxide ($Mn_2O_3$) with the carrier in the presence of a solvent to obtain a mixed product can be changed. Preferably, the above said admixing in solid-phase is carried out under grinding conditions; the above said admixing in the presence of a solvent is performed by dispersing ultrasonically and mechanically. More preferably, when liquid materials are mixed with solid materials, the liquid materials can be admixed with the solid materials by dropwise addition method or by impregnation method, wherein the liquid materials are the solution formed by the precursor of tungstate salt and a solvent, and the solution formed by the precursor of the manganese sesquioxide ($Mn_2O_3$) and a solvent, and the precursor of tungstate salt and the precursor of the manganese sesquioxide ($Mn_2O_3$) all are water-soluable; solid materials are carrier, manganese composite oxide having the perovskite structure and/or the spinel structure, dried mixed product obtained by admixing the precursor of tungstate and/or the precursor of the manganese sesquioxide ($Mn_2O_3$) with the carrier and the manganese composite oxide having the perovskite structure and/or the spinel structure in the presence of a solvent. When admixing the liquid material with the solid materials by means of dropwise addition, the liquid materials can be concurrently added dropwise into the solid material, it is also possible to dropwise add another liquid material after dropwise adding one liquid material completely; the dropping speed of the liquid material is preferably controlled to keep the temperature of the reaction system at 10-30° C.; when admixing the liquid material with the solid materials by means of impregnation method, stepwise impregnation is preferred, the stepwise impregnation method comprising steps of a first impregnation is performed by impregnating the solid materials into one solution, after that, a second impregnation is carried out by impregnating as-impregnated product of the first impregnation into another solution again, wherein the temperature for each impregnation is preferably kept at 30-60° C., the concentration of the solution used for impregnation is preferably controlled at 35-55 wt. %, and the sequence of stepwise impregnation can be changes.

In the present disclosure, the solid admixing refers to physical admixing between solid phase materials in the absence of solvent.

In the present disclosure, for the described preparation method of the catalyst, the mixing sequence of the precursor of tungstate and the precursor of manganese sesquioxide is not specifically specified, anything but that the precursor of tungstate and the precursor of manganese sesquioxide are mixed in solvent in advance and then mixed with other raw materials. Otherwise, when the precursor of manganese sesquioxide and the precursor of tungstate are mixed in the presence of a solvent, neutralization reaction occurs to form plentiful participate that is harmful for the formation of active component and its dispersion. As a result, the crystallinity and dispersibility of tungstate component and manganese sesquioxide component on the surface of the carrier are affected thereby leading to a decline of the catalyst activity.

According to the fifth aspect of the described preparation method of the catalyst, comprising:

1) admixing the manganese composite oxide having the perovskite structure and/or the spinel structure with the carrier in solid-phase to obtain a solid phase admixture A;

2) admixing a precursor of tungstate salt and a precursor of manganese sesquioxide with the solid phase admixture A obtained in step 1) to obtain a admixture B;

3) subsequently drying and calcining the admixture B obtained in step 2).

According to the sixth aspect of the described another preparation method of the catalyst, comprising:

i) admixing a precursor of tungstate salt and a precursor of manganese sesquioxide with the carrier in the presence of a solvent to obtain a mixed product X;

ii) drying the mixed product X obtained in step i) to obtain a dried product Y;

iii) admixing the manganese composite oxide having the perovskite structure and/or the spinel structure with the dried product Y obtained in step ii) in solid-phase and then calcining the obtained mixed product.

The catalyst prepared by the above method, the manganese sesquioxide and the tungstate are supported on the carrier.

According to one embodiment of present disclosure, the method comprising the steps of:

1) admixing the manganese composite oxide having the perovskite structure and/or the spinel structure with the carrier in solid-phase to obtain a solid phase admixture A;

2) admixing a precursor of tungstate salt and the solid phase admixture A of step 1) to obtain a slurry thick paste B;

3) subsequently drying and calcining the slurry thick paste B of step 2).

The catalyst prepared by the above method, the manganese sesquioxide and the tungstate are supported on the manganese composite oxide having the perovskite structure and/or the spinel structure and the carrier.

According to another embodiment of present disclosure, the method comprising the steps of:

i) admixing a precursor of tungstate salt with the carrier in the presence of a solvent to obtain a slurry thick paste X;

ii) admixing the slurry thick paste X of step ii) with a precursor of manganese sesquioxide, and drying the admixture to obtain a dried admixture Y;

iii) admixing the manganese composite oxide having the perovskite structure and/or the spinel structure with the dried admixture Y and subsequently calcining the admixture.

In the preparation method provided by the present disclosure, in order to uniformly admix the materials so as to ensure that the as-obtained admixture has higher specific surface, the solid phase admixing is preferably carried out under grinding conditions, which makes the ground admixture have a particle size varied from 200 to 2000 mesh, further more preferably from 200 to 1000 mesh.

In the preparation method provided by the present disclosure, in order to uniformly admix the materials in case using solvent for obtaining the admixture, preferably the admixing in the presence of a solvent is a stepwise impregnation or ultrasonic agitation mixing; preferably an ultrasonic agitation mixing, and more preferably, the ultrasonic agitation mixing comprises sequentially mixing under ultrasonic and agitation conditions, wherein the ultrasonic condition includes under the ultrasonic power varied from 400 to 2500 W and the ultrasonic frequency varied from 20 to 60 kHz, the mixing time under ultrasonic condition is 0.5-1 hour, and the mixing time under agitation condition is 1-3 hours.

In the preparation method provided by the present disclosure, in order to thoroughly dry the admixture obtained by admixing the slurry thick paste B or the slurry thick paste X with the precursor of manganese sesquioxide, the drying process is performed at temperature varied from 80° C. to 100° C. for time period varied from 1 hour to 2 hours; in order to completely transform the effective components in the admixture into oxides while removing the inevitably formed impurities such as carbon, the calcining treatment of the above dried admixture is performed under oxygen-containing atmosphere at temperature varied from 500° C. to 900° C. for time period from 1 hour to 2 hours; more preferably, oxygen-containing atmosphere is air.

According to the preparation method provided by the present disclosure, in order to effectively exert the synergistic effect of the components for a methane oxidative coupling catalyst having much better catalytic performance, based on 100 parts by weight of the total amount of the precursor of the manganese sesquioxide (calculated by manganese sesquioxide), the precursor of the tungstate, the manganese composite oxide having a perovskite structure and/or a spinel structure, and the carrier, the content of the precursor of the manganese sesquioxide (calculated by manganese sesquioxide) is from over 0 to less than 20 parts by weight and preferably from 1.5 to 18 parts by weight, the content of the precursor of the tungstate is from 1 to 20 parts by weight and preferably from 4 to 18 parts by weight, the content of the manganese composite oxide having the perovskite structure and/or the spinel structure is from 1 to 40 parts by weight and preferably from 2 to 35 parts by weight, and the content of the carrier is from 20 to 98 parts by weight and preferably from 29 to 90 parts by weight.

In the preparation method provided by the present disclosure, the precursors of tungstate salts are water-soluble, which for example can be at least one of sodium tungstate, potassium tungstate and rubidium tungstate and their crystalline hydrates thereof.

In the preparation method provided by the present disclosure, the precursors of manganese sesquioxides are water-soluble, which for example can be at least one of manganese nitrate, manganese acetate, manganese chloride and manganese sulfate and their crystalline hydrates thereof.

In the preparation method provided by the present disclosure, the solvent only needs to dissolve tungstate precursor and manganese trioxide precursor, for example, the solvent can be water. In the presence of solvent, the concentration of tungstate precursor is preferably controlled at 35~45 weight %, and the concentration of manganese sesquioxide precursor is preferably controlled at 35~55 weight %

In the preparation method provided by the present disclosure, for the manganese composite oxide having the perovskite structure and/or the spinel structure, the manganese composite oxide having the perovskite structure and/or the spinel structure comprises at least one element selected from Ti, Fe, Co, Ni, Li, Pb, Cd, Sn, In, Ge, Ga, Sb, Bi, Te, Se, Zr, Hf, V, Nb, Ta, Cr, Mo, W, Ba, Mg, Ce, La, Pr, Nd, Sm, Ca, Sr, Ba, K or combinations thereof.

In the preparation method provided by the present disclosure, preferably, the manganese composite oxide having a perovskite structure and/or a spinel structure is at least one selected from manganese titanate, manganese ferrite, manganese cobaltate, manganese nickelate, lithium manganite, lithium nickel cobalt manganese oxide, manganese plumbite, cadmium acid manganese, manganese stannate, manganese germanate, manganese gallate, bismuth manganate, manganese tellurite, manganese selenate, vanadium manganate, manganese niobate, manganese tantalite, manganese chromate, barium manganate, magnesium manganate, LnAFeMnO6(Ln=La, Pr, Nd, Sm, Ce; A=Ca, Sr, Ba) $La_{0.5}Sr_{0.5}Mn_{1-m}Fe_mO_3$, $Ca_{\alpha}La_{\beta}K_{1-\alpha-\beta}Mn_{0.5}Fe_{0.5}O_3$, $Ca_pLa_qK_{1-p-q}Mn_{0.78}Fe_{0.22}O_3$, $Bi_{0.5}Ca_{0.5-n}La_nFe_{0.3}Mn_{0.7}O_3$, wherein 0<m≤0.25, for example, m can be 0.05, 0.1, 0.12, 0.15, 0.2, 0.22, 0.24, 0.25, and any value between any two of the foregoing adjacent values, 0.1≤m≤0.22, 0≤α≤0.25, for example, α can be 0.05, 0.1, 0.12, 0.15, 0.2, 0.22, 0.24, 0.25, and any value between any two of the foregoing adjacent values; preferably 0.1≤α≤0.2, 0<β≤0.25, for example, β can be 0.05, 0.1, 0.12, 0.15, 0.2, 0.22, 0.24, 0.25, and any value between any two of the foregoing adjacent values; preferably 0.1≤β≤0.2, 0<p≤0.25, for example, p can be 0.05, 0.1, 0.12, 0.15, 0.2, 0.22, 0.24, 0.25, and any value between any two of the foregoing adjacent values; preferably 0.1≤p≤0.2, 0<q≤0.25, for example, q can be 0.05, 0.1, 0.12, 0.15, 0.2, 0.22, 0.24, 0.25, and any value between any two of the foregoing adjacent values; preferably 0.1≤q≤0.2, 0<n≤0.25, for example, n can be 0.05, 0.1, 0.12, 0.15, 0.2, 0.22, 0.24, 0.25, and any value between any two of the foregoing adjacent values; preferably 0.1≤n≤0.2.

In the preparation method provided by the present disclosure, the carrier may be various inorganic heat-resistant oxides and/or carbide that do not adversely affect the catalyst, including but not limited to SiC, $Fe_2O_3$, $Fe_3O_4$, $TiO_2$, $ZrO_2$, $Al_2O_3$, $La_2O_3$, CaO, SrO, MgO, $SiO_2$ or combinations thereof. On the one hand, $SiO_2$ is economical; on the other hand, $SiO_2$ can be transformed into cristobalite phase that is beneficial to the catalytic activity of the catalyst. Hence, $SiO_2$ is preferably chosen as the carrier.

In the preparation method provided by the present disclosure, preferably, the carrier comprises particles having a size varied from 100 to 2000 mash, even more preferably from 100 to 1000 mesh; preferably, the carrier comprises particles having the specific surface varied from 10 to 1000 m²/g, even more preferably, from 50 to 250 m²/g; preferably, the carrier comprises particles having the pore volume varied from 0.1 to 1.2 mL/g, even more preferably, from 0.5 to 0.9 mL/g; preferably, the carrier comprises particles having the most probable pore size varied from 2.0 to 20 nm, even more preferably, from 2.0 to 10.0 nm. In this way, the carrier can be guaranteed to have higher specific surface area and provide more active sites thereby leading to improved catalytic performance of the catalyst. In the present disclosure, the specific surface and pore volume refer to BET specific surface and pore volume, and the most probable pore size is calculated from the adsorption curve using BJH (Barrett-Joyner-Halenda) model.

In the preparation method provided by the present disclosure, the manganese composite oxide having the perovskite structure and/or the spinel structure comprises particles having size varied from 100 to 2000 mash, preferably, from 100 to 1000 mesh.

The seventh aspect of the present disclosure also provides a catalyst obtained by the specific implementation method of the above preparation method.

For the catalyst obtained by the preparation method provided by the present disclosure, the catalyst has a composition represented by a general formula $xMn_2O_3$-$yR_2WO_4$-$zMn_rM^1_{s1}M^2_{s2}\ldots M^n_{sn}O_t$-(100-x-y-z)Support, wherein R represents an alkali metal element selected from Na, K, and Rb; Support represents the carrier; $Mn_rM^1_{s1}M^2_{s2}\ldots M^n_{sn}O_t$, of which the elements are arranged in any order, represents the composition of the manganese composite oxide having the perovskite structure and/or the spinel structure, wherein $M^1, M^2, \ldots M^n$ represent the elements except manganese in the manganese composite oxide with perovskite structure and/or spinel structure, and are selected from at least one of Ti, Fe, Co, Ni, Li, Pb, Cd, Sn, In, Ge, Ga, Sb, Bi, Te, Se, Zr, Hf, V, Nb, Ta, Cr, Mo, W, Mg, Ba, Ce, La, Pr, Nd, Sm, Ca, Sr, Ba, K; in the general formula for the manganese composite oxide having the perovskite structure and/or the spinel structure, r represents the number of manganese atoms, s1, s2, ... sn respectively represents the number of $M^1, M^2, \ldots M^n$ atoms, t represents the number of oxygen atoms, wherein 0<r≤1, 0≤s1≤1, 0≤s2≤1, ..., 0≤sn≤1, 1≤t≤6; the x, y, and z respectively represents the weight fraction occupied by the manganese sesquioxide, the tungstate, and the manganese composite oxide having the perovskite structure and/or the spinel structure; in the general formula, the connection symbols between the components have no special meaning, and the arrangement sequence of the components is not in any order. The general formula of the catalyst only represents that the weight fractions of x, y, z and (100-x-y-z) respectively occupied by the manganese sesquioxide ($Mn_2O_3$), the tungstate ($R_2WO_4$), the manganese composite oxide ($Mn_rM^1_{s1}M^2_{s2}\ldots M^n_{sn}O_t$) having a perovskite structure and/or a spinel structure, and the carrier (Support). As each component formed in the preparation process of the catalyst does not involve any weight loss, the weight fraction of each component in the catalyst is calculated according to the feeding amount of the raw material source of each component.

The eighth aspect of the present disclosure also provides the application of above-mentioned catalyst or the catalyst obtained by the specific implementation method of the above preparation method in oxidative coupling of methane.

The ninth aspect of the present disclosure also provides a method for oxidative coupling of methane, comprising: bringing a catalyst into contact with a feed gas stream containing methane and oxygen to have the methane reacting with oxygen under oxidative coupling of methane conditions, wherein the catalyst is the each one chosen from the above described catalysts or the catalysts obtained by the above described preparation method.

According to the method for oxidative coupling of methane provided by the present disclosure, the methane to oxygen volume ratio in the feed gas stream is 3:1~8:1; the reaction temperature is from 620 to 900° C., for example, 620° C., 630° C., 640° C., 650° C., 660° C., 670° C., 680° C., 690° C., 700° C., 720° C., 750° C., 780° C., 800° C., 820° C., 850° C. 880° C., and 900° C., and any temperature between any two of the aforementioned adjacent temperatures, preferably from 620 to 800° C.; the reaction pressure is from 0.1 to 2 MPa, preferably from 0.1 to 1 MPa; on the basis of the total amount of methane and oxygen, the gas hourly space velocity is from 3000-50000 mL·h$^{-1}$·g$^{-1}$, preferably from 4000-8500 mL·h$^{-1}$·g$^{-1}$.

According to the present disclosure, in the reaction process of oxidative coupling of methane between methane and oxygen, inert gas can be used to dilute the feed gas composed of methane and oxygen, in order to avoid fast temperature rise in the reaction process of oxidative coupling of methane and to eliminate thermal effect, wherein the inert gas can be nitrogen or helium, and nitrogen is preferable; more preferably, the volume ratio of the methane, oxygen and the inert gas can be 3~8:1:3.5~4.5.

According to the method for oxidative coupling of methane provided by the present disclosure, in the reaction process of oxidative coupling of methane, since the catalyst used is the aforementioned catalyst provided by the present disclosure or catalyst obtained by the specific implementation method of the above preparation method provided by the present disclosure, the temperature for oxygen molecule activation in oxidative coupling of methane can be effectively reduced, thereby leading to a significant reduction of the reaction temperature from 800-900° C. for the traditional catalysts to less than 700° C., preferably 620~700° C.

The present disclosure will be described in further detail and fully with reference to the embodiments and drawings.

In the following Experimental Examples and Experimental Comparative Examples, the manganese titanate has a particle size of 500 mesh, the manganese ferrite has a particle size of 200 mesh, the manganese cobaltate has a particle size of 200 mesh, the Ca$_{0.2}$La$_{0.2}$K$_{0.6}$Mn$_{0.78}$Fe$_{0.22}$O$_3$ has a particle size of 325 mesh.

In the following Experimental Examples and Experimental Comparative Examples, the carrier is SiO$_2$, which has a particle size of 200 mesh, specific surface area of 50~250 m$^2$/g, pore volume of 0.5~0.9 mL/g, and most probable pore size of 2.0~10.0 nm.

In the following Experimental Examples and Experimental Comparative Examples, X-ray diffraction analysis was carried out on a Rigaku Uitima IV X-ray diffractometer from Japan Science Company; analysis of pore structure parameters of the carrier is carried out on an Autosorb-3B gas adsorption instrument from Quantachrome Instruments; the specific surface area and pore volume of the samples were measured by BET nitrogen adsorption method; the most probable pore size is calculated from the adsorption curve using BJH (Barrett-Joyner-Halenda) model; the loading amount of each active component in the catalyst is measured by means of X-ray powder diffraction standard working curve method carried out on a Rigaku Uitima IV X-ray diffractometer from Japan Science Company.

In the following Application Examples, the analysis of the components of the reaction products is carried out on an Agilent 7820A gas chromatograph.

In the following Experimental Examples and Experimental Comparative Examples, ultrasonic dispersing is carried out using an ultra-sonic homogenizer purchased from Shanghai Kudos ultrasonic instrument Co., Ltd., with ultrasonic power of 400-500 W and ultrasonic frequency of 25 kHz.

In the following Experimental Examples and Experimental Comparative Examples, admixing the raw materials is carried out at room temperature.

In the following Experimental Examples and Experimental Comparative Examples, methane conversion and product selectivity were calculated using the standard normalization method on the basis of carbon atom balance and defined as follows:

Conversion=$[1-C_{methane,outlet}/(C_{methane,outlet}+C_{CO,outlet}+C_{CO2,outlet}+2C_{total\ amount\ of\ ethylene\ and\ ethane,outlet}+3C_{total\ amount\ of\ propylene\ propane,outlet})] \times 100\%$;

Selectivity=$[n \times C_{Carbon-containing\ product,outlet}/(C_{CO,outlet}+C_{CO2,outlet}+2C_{total\ amount\ of\ ethylene\ and\ ethane,outlet}+3C_{total\ amount\ of\ propylene\ propane,outlet}] \times 100\%$, wherein n is the number of carbon atom in the each carbon-containing product, C is the volume concentration of each carbon-containing product at the outlet.

Example 1

The purpose of this example is to provide a catalyst: 3Mn$_2$O$_3$-10Na$_2$WO$_4$-10MnTiO$_3$-77SiO$_2$, the preparation method is as follows:

1) 1.54 grams of dried SiO$_2$ powder (particle size of 200 mesh, specific surface area of 200 m$^2$/g, pore volume of 0.9 mL/g, most probable pore size of 2 nm) and 0.2 grams of manganese titanate powder were weighed, admixed and ground thoroughly, after that, the admixture was transferred into a 100 mL beaker. 0.2 grams of Na$_2$WO$_4$·2H$_2$O were weighed and dissolved into 5.0 mL deionized water to obtain an aqueous solution of sodium tungstate. To the above-obtained dried admixture comprising 1.54 grams of SiO$_2$ and 0.2 g manganese titanate was dropwise added the as-prepared aqueous solution of sodium tungstate by controlling the adding rate to have the system temperature kept at 10-30° C., followed by dispersing the admixture ultrasonically for 1 hour and subsequently mechanically stirring for 3 hours to have the consistency of a slurry thick paste;

2) 0.272 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 3 hours and subsequently drying the admixture at 100° C. to obtain a dried admixture;

3) the dried admixture of step 2) was ground to powder and the ground powder was calcined in an air atmosphere at 550° C. for 2 hours to obtain the catalyst of the present example.

FIG. 1 presents the X-ray diffraction patterns of 3Mn$_2$O$_3$-10Na$_2$WO$_4$-10MnTiO$_3$-77SiO$_2$ catalyst as prepared in example 1; as shown in FIG. 1, the catalyst comprises three phases of Mn$_2$O$_3$, Na$_2$WO$_4$, and MnTiO$_3$.

Example 2

The purpose of this example is to provide a catalyst: 5Mn$_2$O$_3$-5Na$_2$WO$_4$-8MnTiO$_3$-82SiO$_2$, the preparation method is as follows:

1) 1.64 grams of dried $SiO_2$ powder (particle size of 200 mesh, specific surface area of 235 $m^2/g$, pore volume of 0.8 mL/g, most probable pore size of 6.0 nm) were weighed and transferred into a 100 mL beaker. 0.1 grams of $Na_2WO_4 \cdot 2H_2O$ were weighed and dissolved into 5.0 mL deionized water to obtain an aqueous solution of sodium tungstate. To the dried $SiO_2$ powder was dropwise added the as-prepared aqueous solution of sodium tungstate by controlling the adding rate to have the system temperature kept at 10-30° C., followed by dispersing the admixture ultrasonically for 0.6 hour and subsequently mechanically stirring for 2 hours to have the consistency of a slurry thick paste;

2) 0.453 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 1 hour and subsequently drying the admixture at 90° C. to obtain a dried admixture;

3) the dried admixture of step 2) was admixed with 0.16 grams of manganese titanate powder, and the admixture was ground to powder and calcined in an air atmosphere at 650° C. for 2 hours to obtain the catalyst of the present example.

Figure 2:
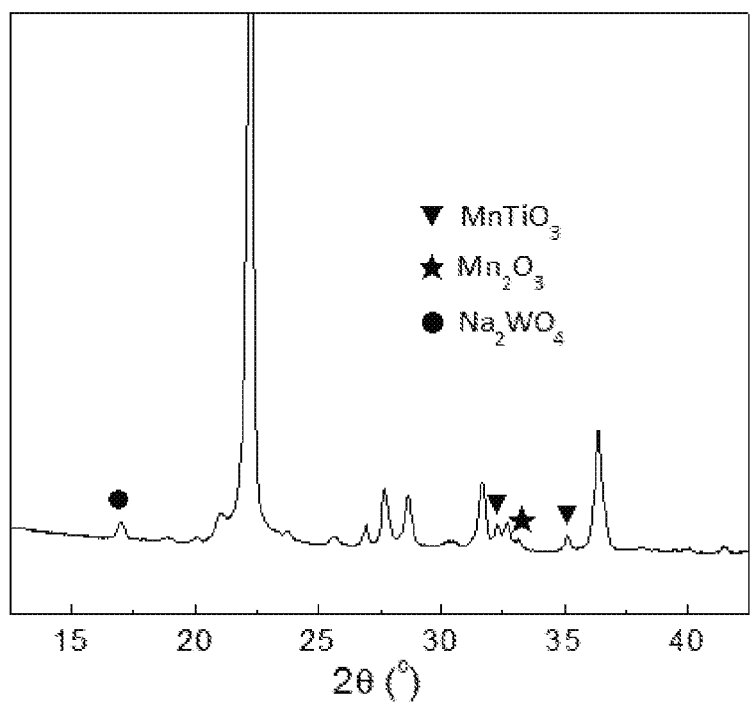
FIG. 2 is the X-ray diffraction pattern of $5Mn_2O_3$-$5Na_2WO_4$-$8MnTiO_3$-$82SiO_2$ catalyst as prepared in Example 2.

FIG. 2 presents the X-ray diffraction patterns of $5Mn_2O_3$-$5Na_2WO_4$-$8MnTiO_3$-$82SiO_2$ catalyst as prepared in example 2; as shown in FIG. 2, the catalyst comprises three phases of $Mn_2O_3$, $Na_2WO_4$, and $MnTiO_3$.

Example 3

The purpose of this example is to provide a catalyst: $1.5Mn_2O_3$-$8Na_2WO_4$-$4MnTiO_3$-$86.5SiO_2$, the preparation method is as follows:

1) 1.73 grams of dried $SiO_2$ powder (particle size of 200 mesh, specific surface area of 220 $m^2/g$, pore volume of 0.9 mL/g, most probable pore size of 7.0 nm) and 0.8 grams of manganese titanate powder were weighed respectively and transferred into a 100 mL beaker; 0.16 grams of $Na_2WO_4 \cdot 2H_2O$ were weighed and dissolved into 5.0 mL deionized water to obtain an aqueous solution of sodium tungstate. To the above-obtained dried admixture comprising 1.73 grams of $SiO_2$ and 0.8 g manganese titanate was dropwise added the as-prepared aqueous solution of sodium tungstate by controlling the adding rate to have the system temperature kept at 10-30° C., followed by dispersing the admixture ultrasonically for 1 hour and subsequently mechanically stirring for 1 hour to have the consistency of a slurry thick paste;

2) 0.136 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 2 hours and subsequently drying the admixture at 80° C. to obtain a dried admixture;

3) the dried admixture of step 2) was ground to powder and the ground powder was calcined in an air atmosphere at 500° C. for 1.5 hours to obtain the catalyst of the present example.

As indicated by X-ray powder diffraction analysis, three phases of $Mn_2O_3$, $Na_2WO_4$, and $MnTiO_3$ were clearly observed in the X-ray diffraction patterns of the catalyst of the present example.

Example 4

The purpose of this example is to provide a catalyst: $10Mn_2O_3$-$4Na_2WO_4$-$5MnTiO_3$-$83SiO_2$, the preparation method is as follows:

1) 1.66 grams of dried $SiO_2$ powder (particle size of 200 mesh, specific surface area of 225 $m^2/g$, pore volume of 0.5 mL/g, most probable pore size of 10.0 nm) and 0.1 grams of manganese titanate powder were weighed respectively and transferred into a 100 mL beaker; 0.08 grams of $Na_2WO_4 \cdot 2H_2O$ were weighed and dissolved into 5.0 mL deionized water to obtain an aqueous solution of sodium tungstate. To the above-obtained dried admixture comprising 1.66 grams of $SiO_2$ and 0.1 g manganese titanate was dropwise added the as-prepared aqueous solution of sodium tungstate by controlling the adding rate to have the system temperature kept at 10-30° C., followed by dispersing the admixture ultrasonically for 0.6 hour and subsequently mechanically stirring for 2.5 hours to have the consistency of a slurry thick paste;

2) 0.906 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 3 hours and subsequently drying the admixture at 100° C. to obtain a dried admixture;

3) the dried admixture of step 2) was ground to a powder and the ground powder was calcined in an air atmosphere at 700° C. for 2 hours to obtain the catalyst of the present example.

As indicated by X-ray powder diffraction analysis, three phases of $Mn_2O_3$, $Na_2WO_4$, and $MnTiO_3$ were clearly observed in the X-ray diffraction patterns of the catalyst of the present example.

Example 5

The purpose of this example is to provide a catalyst: $15Mn_2O_3$-$12Na_2WO_4$-$20MnTiO_3$-$53SiO_2$, the preparation method is as follows:

1) 1.06 grams of dried $SiO_2$ powder (particle size of 200 mesh, specific surface area of 210 $m^2/g$, pore volume of 0.6 mL/g, most probable pore size of 5.5 nm) were weighed and transferred into a 100 mL beaker; 0.24 grams of $Na_2WO_4 \cdot 2H_2O$ were weighed and dissolved into 5.0 mL deionized water to obtain an aqueous solution of sodium tungstate. To the dried $SiO_2$ powder was dropwise added the as-prepared aqueous solution of sodium tungstate by controlling the adding rate to have the system temperature kept at 10-30° C., followed by dispersing the admixture ultrasonically stirring for 0.7 hour and subsequently mechanically for 2.0 h to have the consistency of a slurry thick paste;

2) 1.360 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10~30° C.

followed by stirring the admixture mechanically for 1.5 hours and subsequently drying the admixture at 80° C. to obtain a dried admixture;

3) the dried admixture of step 2) was admixed with 0.4 grams of manganese titanate powder, and the admixture was ground to powder and calcined in an air atmosphere at 800° C. for 1 hour to obtain the catalyst of the present example.

As indicated by X-ray powder diffraction analysis, three phases of $Mn_2O_3$, $Na_2WO_4$, and $MnTiO_3$ were clearly observed in the X-ray diffraction patterns of the catalyst of the present example.

Example 6

The purpose of this example is to provide a catalyst: $18Mn_2O_3\text{-}15Na_2WO_4\text{-}15MnTiO_3\text{-}52SiO_2$, the preparation method is as follows:

1) 1.04 grams of dried $SiO_2$ powder (particle size of 200 mesh, specific surface area of 205 $m^2/g$, pore volume of 0.75 mL/g, most probable pore size of 2.5 nm) were weighed and transferred into a 100 mL beaker; 0.3 grams of $Na_2WO_4.2H_2O$ were weighed and dissolved into 5.0 mL deionized water to obtain an aqueous solution of sodium tungstate. To the dried $SiO_2$ powder was dropwise added the as-prepared aqueous solution of sodium tungstate by controlling the adding rate to have the system temperature kept at 10-30° C., followed by dispersing the admixture ultrasonically for 0.9 hour and subsequently mechanically for 2.5 hours to have the consistency of a slurry thick paste;

2) 1.632 grams of aqueous solution of manganese nitrate with a concentration of 50 weight % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 1 hour and subsequently drying the admixture at 100° C. to obtain a dried admixture;

3) the dried admixture of step 2) was admixed with 0.3 grams of manganese titanate powder, and the admixture was ground to powder and calcined in an air atmosphere at 800° C. for 2.5 hours to obtain the catalyst of the present example.

As indicated by X-ray powder diffraction analysis, three phases of $Mn_2O_3$, $Na_2WO_4$, and $MnTiO_3$ were clearly observed in the X-ray diffraction patterns of the catalyst of the present example.

Example 7

The purpose of this example is to provide a catalyst: $2Mn_2O_3\text{-}18Na_2WO_4\text{-}7MnTiO_3\text{-}73SiO_2$, the preparation method is as follows:

1) 1.46 grams of dried $SiO_2$ powder (particle size of 200 mesh, specific surface area of 215 $m^2/g$, pore volume of 0.69 mL/g, most probable pore size of 4.5 nm) and 0.14 grams of manganese titanate powder were weighed respectively, ground thoroughly, and transferred into a 100 mL beaker; 0.36 grams of $Na_2WO_4.2H_2O$ were weighed and dissolved into 5.0 mL deionized water to obtain an aqueous solution of sodium tungstate. To the above-obtained dried admixture comprising 1.46 grams of $SiO_2$ and 0.14 g manganese titanate was dropwise added the as-prepared aqueous solution of sodium tungstate by controlling the adding rate to have the system temperature kept at 10–30° C., followed by dispersing the admixture ultrasonically for 0.8 hour and subsequently mechanically stirring for 3 hours to have the consistency of a slurry thick paste;

2) 0.181 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 1.5 hours and subsequently drying the admixture at 90° C. to obtain a dried admixture;

3) the dried admixture of step 2) was ground to powder and the ground powder was calcined in an air atmosphere at 650° C. for 2 hours to obtain the catalyst of the present example.

As indicated by X-ray powder diffraction analysis, three phases of $Mn_2O_3$, $Na_2WO_4$, and $MnTiO_3$ were clearly observed in the X-ray diffraction patterns of the catalyst of the present example.

Example 8

The purpose of this example is to provide a catalyst: $12Mn_2O_3\text{-}10Na_2WO_4\text{-}2MnTiO_3\text{-}76SiO_2$, the preparation method is as follows:

1) 1.52 grams of dried $SiO_2$ powder (particle size of 200 mesh, specific surface area of 212 $m^2/g$, pore volume of 0.7 mL/g, most probable pore size of 2.3 nm) were weighed and transferred into a 100 mL beaker; 0.2 grams of $Na_2WO_4.2H_2O$ were weighed and dissolved into 5.0 mL deionized water to obtain an aqueous solution of sodium tungstate. To the dried $SiO_2$ powder was dropwise added the as-prepared aqueous solution of sodium tungstate by controlling the adding rate to have the system temperature kept at 10-30° C., followed by dispersing the admixture ultrasonically for 0.9 h and subsequently mechanically stirring for 1.5 hours to have the consistency of a slurry thick paste;

2) 1.088 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 2.5 hours and subsequently drying the admixture at 85° C. to obtain a dried admixture;

3) the dried admixture of step 2) was admixed with 0.04 grams of manganese titanate powder, and the admixture was ground to powder and calcined in an air atmosphere at 900° C. for 2 hours to obtain the catalyst of the present example.

As indicated by X-ray powder diffraction analysis, three phases of $Mn_2O_3$, $Na_2WO_4$, and $MnTiO_3$ were clearly observed in the X-ray diffraction patterns of the catalyst of the present example.

Example 9

The purpose of this example is to provide a catalyst: $8Mn_2O_3\text{-}12Na_2WO_4\text{-}28MnTiO_3\text{-}52SiO_2$, the preparation method is as follows:

1) 1.24 grams of dried $SiO_2$ powder (particle size of 200 mesh, specific surface area of 300 $m^2/g$, pore volume of 1.2 mL/g, most probable pore size of 12 nm) and 0.56 grams of manganese titanate powder were weighed respectively, ground thoroughly, and transferred into a 100 mL beaker; 0.24 grams of $Na_2WO_4.2H_2O$ were weighed and dissolved into 5.0 mL deionized water to obtain an aqueous solution of sodium tungstate. To the above-obtained dried admixture comprising 1.24 grams of $SiO_2$ and 0.56 g manganese titanate was dropwise added the as-prepared aqueous solution of sodium tungstate by controlling the adding rate to have the system temperature kept at 10-30° C., followed by dispersing the admixture ultrasonically for 0.5 hour and subsequently mechanically stirring for 1.5 hours to have the consistency of a slurry thick paste;

2) 0.725 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 2 hours and subsequently drying the admixture at 100° C. to obtain a dried admixture;

3) the dried admixture of step 2) was ground to powder and the ground powder was calcined in an air atmosphere at 750° C. for 2 hours to obtain the catalyst of the present example.

As indicated by X-ray powder diffraction analysis, three phases of $Mn_2O_3$, $Na_2WO_4$, and $MnTiO_3$ were clearly observed in the X-ray diffraction patterns of the catalyst of the present example.

Example 10

The purpose of this example is to provide a catalyst: $18Mn_2O_3$-$18Na_2WO_4$-$35MnTiO_3$-$29SiO_2$, the preparation method is as follows:

1) 0.58 grams of dried $SiO_2$ powder (particle size of 200 mesh, specific surface area of 245 m$^2$/g, pore volume of 0.6 mL/g, most probable pore size of 12 nm) were weighed and transferred into a 100 mL beaker; 0.36 grams of $Na_2WO_4.2H_2O$ were weighed and dissolved into 5.0 mL deionized water to obtain an aqueous solution of sodium tungstate. To the dried $SiO_2$ powder was dropwise added the as-prepared aqueous solution of sodium tungstate by controlling the adding rate to have the system temperature kept at 10-30° C., followed by dispersing the admixture ultrasonically for 0.6 hour and subsequently mechanically stirring for 2.5 hours to have the consistency of a slurry thick paste;

2) 1.632 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 2 hours and subsequently drying the admixture at 95° C. to obtain a dried admixture;

3) the dried admixture of step 2) was admixed with 0.7 grams of manganese titanate powder, and the admixture was ground to powder and calcined in an air atmosphere at 850° C. for 2 hours to obtain the catalyst of the present example.

As indicated by X-ray powder diffraction analysis, three phases of $Mn_2O_3$, $Na_2WO_4$, and $MnTiO_3$ were clearly observed in the X-ray diffraction patterns of the catalyst of the present example.

Example 11

The purpose of this example is to provide a catalyst: $3Mn_2O_3$-$10Na_2WO_4$-$10MnFe_2O_4$-$77SiO_2$, the preparation method is as follows:

1) 1.54 grams of dried $SiO_2$ powder (particle size of 200 mesh, specific surface area of 205 m$^2$/g, pore volume of 1.1 mL/g, most probable pore size of 6.5 nm) and 0.2 grams of manganese ferrite powder were weighed respectively, ground thoroughly, and transferred into a 100 mL beaker; 0.2 grams of $Na_2WO_4.2H_2O$ were weighed and dissolved into 5.0 mL deionized water to obtain an aqueous solution of sodium tungstate. To the above-obtained dried admixture comprising 1.54 grams of $SiO_2$ and 0.2 g manganese ferrite was dropwise added the as-prepared aqueous solution of sodium tungstate by controlling the adding rate to have the system temperature kept at 10-30° C., followed by dispersing the admixture ultrasonically for 1 hour and subsequently mechanically stirring for 3 hours to have the consistency of a slurry thick paste;

2) 0.272 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C. followed by stirring the admixture mechanically for 3 hours and subsequently drying the admixture at 100° C. to obtain a dried admixture;

3) the dried admixture of step 2) was ground to powder and the ground powder was calcined in an air atmosphere at 550° C. for 2 hours to obtain the catalyst of the present example.

As indicated by X-ray powder diffraction analysis, three phases of $Mn_2O_3$, $Na_2WO_4$, and $MnFe_2O_4$ were clearly observed in the X-ray diffraction patterns of the catalyst of the present example.

Example 12

The purpose of this example is to provide a catalyst: $5Mn_2O_3$-$5Na_2WO_4$-$8MnCo_2O_4$-$82SiO_2$, the preparation method is as follows:

1) 1.64 grams of dried $SiO_2$ powder (particle size of 200 mesh, specific surface area of 234 m$^2$/g, pore volume of 0.8 mL/g, most probable pore size of 5.5 nm) were weighed and transferred into a 100 mL beaker; 0.1 grams of $Na_2WO_4.2H_2O$ were weighed and dissolved into 5.0 mL deionized water to obtain an aqueous solution of sodium tungstate. To the dried $SiO_2$ powder was dropwise added the as-prepared aqueous solution of sodium tungstate by controlling the adding rate to have the system temperature kept at 10-30° C., followed by dispersing the admixture ultrasonically for 0.6 hour and subsequently mechanically stirring for 2 hours to have the consistency of a slurry thick paste;

2) 0.453 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 1 hour and subsequently drying the admixture at 90° C. to obtain a dried admixture;

3) the dried admixture of step 2) was admixed with 0.16 grams of manganese cobaltate powder, and the admixture was ground to powder and calcined in an air atmosphere at 650° C. for 2 hours to obtain the catalyst of the present example.

As indicated by X-ray powder diffraction analysis, three phases of $Mn_2O_3$, $Na_2WO_4$, and $MnCo_2O_4$ were clearly observed in the X-ray diffraction patterns of the catalyst of the present example.

Example 13

The purpose of this example is to provide a catalyst: $1.5Mn_2O_3\text{-}8K_2WO_4\text{-}4\ MnLi_2O_4\text{-}86.5SiO_2$, the preparation method is as follows:

1) 1.73 grams of dried $SiO_2$ powder (particle size of 200 mesh, specific surface area of 234 m$^2$/g, pore volume of 0.8 mL/g, most probable pore size of 5.5 nm) and 0.8 grams of lithium manganate powder were weighed respectively, ground thoroughly, and transferred into a 100 mL beaker; 0.16 grams of $K_2WO_4\cdot 2H_2O$ were weighed and dissolved into 5.0 mL deionized water to obtain an aqueous solution of sodium tungstate. To the above-obtained dried admixture comprising 1.73 grams of $SiO_2$ and 0.8 grams lithium manganate was dropwise added the as-prepared aqueous solution of sodium tungstate by controlling the adding rate to have the system temperature kept at 10-30° C., followed by dispersing the admixture ultrasonically for 1 hour and subsequently mechanically stirring for 1 hour to have the consistency of a slurry thick paste;

2) 0.136 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 2 hours and subsequently drying the admixture at 80° C. to obtain a dried admixture;

3) the dried admixture of step 2) was ground to powder and the ground powder was calcined in an air atmosphere at 500° C. for 1.5 hours to obtain the catalyst of the present example.

As indicated by X-ray powder diffraction analysis, three phases of $Mn_2O_3$, $K_2WO_4$, and $MnLi_2O_4$ were clearly observed in the X-ray diffraction patterns of the catalyst of the present example.

Example 14

The purpose of this example is to provide a catalyst: $3Mn_2O_3\text{-}10Na_2WO_4\text{-}10\ Ca_{0.2}La_{0.2}K_{0.6}Mn_{0.78}Fe_{0.22}O_3\text{-}77SiO_2$, the preparation method is as follows:

1) 1.54 grams of dried $SiO_2$ powder (particle size of 200 mesh, specific surface area of 228 m$^2$/g, pore volume of 0.7 mL/g, most probable pore size of 7.5 nm) and 0.22 grams of $Ca_{0.2}La_{0.2}K_{0.6}Mn_{0.78}Fe_{0.22}O_3$ (obtained by sol-gel method, according to Journal of Materials Science 2014, 49: 6883-6891) powder were weighed respectively, ground thoroughly, and transferred into a 100 mL beaker; 0.2 grams of $Na_2WO_4\cdot 2H_2O$ were weighed and dissolved into 5.0 mL deionized water to obtain an aqueous solution of sodium tungstate. To the above-obtained dried admixture comprising 1.54 grams of $SiO_2$ and 0.22 grams of $Ca_{0.2}La_{0.2}K_{0.6}Mn_{0.78}Fe_{0.22}Fe_{0.22}O_3$ was dropwise added the as-prepared aqueous solution of sodium tungstate by controlling the adding rate to have the system temperature kept at 10-30° C., followed by dispersing the admixture ultrasonically for 1 hour and subsequently mechanically stirring for 3 hours to have the consistency of a slurry thick paste;

2) 0.272 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 3 hours and subsequently drying the admixture at 100° C. to obtain a dried admixture;

3) the dried admixture of step 2) was ground to powder and the ground powder was calcined in an air atmosphere at 550° C. for 2 hours to obtain the catalyst of the present example.

As indicated by X-ray powder diffraction analysis, three phases of $Mn_2O_3$, $Na_2WO_4$, and $Ca_{0.2}La_{0.2}K_{0.6}Mn_{0.78}Fe_{0.22}O_3$ were clearly observed in the X-ray diffraction patterns of the catalyst of the present example.

Comparative Example 1

The purpose of this comparative example is to provide a catalyst: $3Mn_2O_3\text{-}10Na_2WO_4\text{-}87SiO_2$, according to the method of Example 1, wherein the difference is that manganese titanate is not added in the preparation process, specifically the preparation method is as follows:

1) 1.74 grams of dried amorphous $SiO_2$ powder (particle size of 200 mesh, specific surface area of 200 m$^2$/g, pore volume of 0.9 mL/g, most probable pore size of 2.0 nm) were weighed and transferred into a 100 mL beaker; 0.2 grams of $Na_2WO_4\cdot 2H_2O$ were weighed and dissolved into 5.0 mL deionized water to obtain an aqueous solution of sodium tungstate. To the dried amorphous $SiO_2$ powder was dropwise added the as-prepared aqueous solution of sodium tungstate, followed by dispersing the admixture ultrasonically for 1 hour and subsequently mechanically stirring for 3 hours to have the consistency of a slurry thick paste;

2) 0.272 grams of aqueous solution of manganese nitrate with a concentration of 50 wt. % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by stirring the admixture mechanically for 3 hours and subsequently drying the admixture at 100° C. to obtain a dried admixture;

3) the dried admixture of step 2) was ground to powder and the ground powder was calcined in an air atmosphere at 550° C. for 2 hours to obtain the catalyst of the present comparative example.

Comparative Example 2

The purpose of this comparative example is to provide a catalyst: $3Mn_2O_3\text{-}10Na_2WO_4\text{-}87$Sillicalite-1, according to the method of Example 1, wherein the difference is that manganese titanate is not added in the preparation process and MFI-type full-silica Sillicalite-1 zeolite is used to replace $SiO_2$ as carrier, specifically the preparation method is as follows:

1) 1.74 grams of dried MFI-type full-silica Sillicalite-1 zeolite powder (particle size of 1000 mesh, specific surface area of 320 m$^2$/g, pore volume of 0.2 mL/g) were weighed and transferred into a 100 mL beaker; 0.2 grams of $Na_2WO_4\cdot 2H_2O$ were weighed and dissolved into 5.0 mL deionized water to obtain an aqueous solution of sodium tungstate. To the MFI-type full-silica Sillicalite-1 zeolite powder was dropwise added the as-prepared aqueous solution of sodium tungstate, followed by dispersing the admixture ultrasonically for 0.6 hour and subsequently mechanically stirring for 2 hours to have the consistency of a slurry thick paste;

2) 0.272 grams of aqueous solution of manganese nitrate with a concentration of 50 weight % was weighed and diluted to 5 mL by adding deionized water. To the slurry thick paste of step 1) was dropwise added the aqueous solution of manganese nitrate under stirring by controlling the adding rate to have the system temperature kept at 10-30° C., followed by homogenizing the admixture mechanically for 1 hour and subsequently drying the admixture at 90° C. to obtain a dried admixture;

3) the dried admixture of step 2) was ground to powder and the ground powder was calcined in an air atmosphere at 650° C. for 2 hours to obtain the catalyst of the present comparative example.

Figure 3:
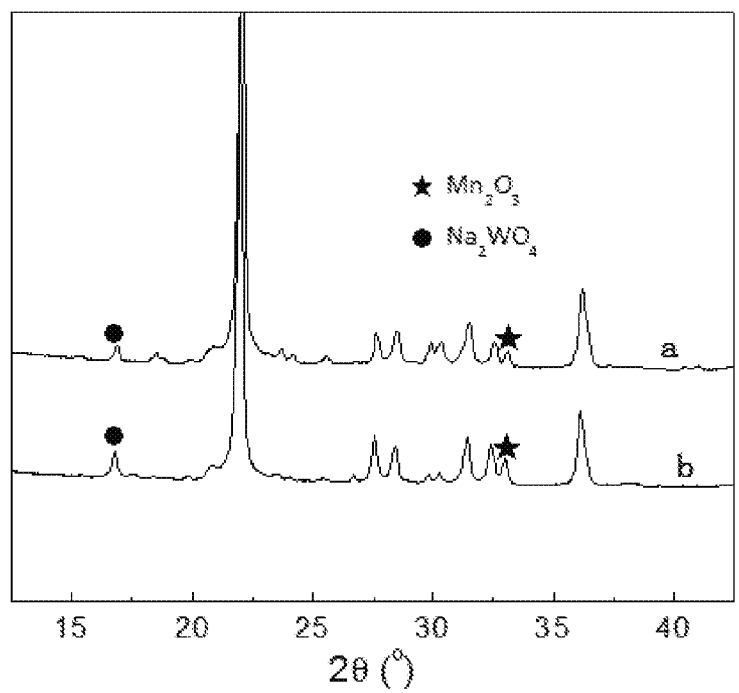
FIG. 3 is the X-ray diffraction pattern of $3Mn_2O_3$-$10Na_2WO_4$-$87SiO_2$ catalyst as prepared in Comparative Example 1 and the X-ray diffraction pattern of $3Mn_2O_3$-$10Na_2WO_4$-87Sillicalite-1 catalyst as prepared in Comparative Example 2, wherein pattern a represents the X-ray diffraction pattern of the catalyst as prepared in Comparative Example 1 and pattern b represents the X-ray diffraction pattern of the catalyst as prepared in Comparative Example 2.

FIG. 3 presents the X-ray diffraction patterns of (a) $3Mn_2O_3$-$10Na_2WO_4$-$87SiO_2$ catalyst as prepared in comparative example 1 and (b) $3Mn_2O_3$-$10Na_2WO_4$-$87Sillicalite$-1 catalyst as prepared in comparative example 2. As shown in FIG. 3, only $Mn_2O_3$ and $Na_2WO_4$ phases rather than $MnTiO_3$ phase are detected for these two comparative catalyst samples by XRD.

Comparative Example 3

Referring to the EXAMPLE 2 of CN201410001437.7, the purpose of this comparative example is to provide a catalyst: $4.2MnO_2 \cdot 1.5Na_2O \cdot 5.5WO_3 \cdot 2.9TiO_2 \cdot 85.9SiO_2$.

As indicated by X-ray powder diffraction analysis, only the diffraction peaks same as the Ti-MWW zeolite but not the others were clearly observed, in the X-ray diffraction (XRD) patterns of the catalyst of the present comparative example.

Application Example 1

The catalyst reaction evaluation was carried out on a continuous flow fixed bed quartz tube reactor, a 400 mm of straight cylindrical tubing with an internal diameter of 16 mm. The catalyst bed height is 10 mm. The catalyst was heated to the set reaction temperature and directly exposed without pretreatment, the feed gas was then introduced into the catalyst bed for reaction. After condensation and separation of condensable products from reaction tail gas by frozen ethanol-water bath (30% ethanol), the effluent gas was analyzed with an online gas chromatograph equipped with a TCD, using a 60 m DM-Plot Msieve 5A column (DIKMA, for the separation of $N_2$, $O_2$, CO, and $CH_4$) and a 30 m DM-Plot Q capillary column (DIKMA, for the separation of $CO_2$, $CH_4$, $C_2H_4$, $C_2H_6$, $C_3H_6$, and $C_3H_8$) in parallel.

The purpose of this application example is to investigate the catalytic performance of the catalysts obtained by the examples and comparative examples in oxidative coupling of methane at different reaction temperatures. The catalyst evaluation was carried out under atmospheric pressure at 620-700° C. and a gas hourly space velocity (GHSV) of 8000 mL·h$^{-1}$·g$^{-1}$ (calculated by methane and oxygen), using a gaseous mixture of $CH_4$:$O_2$:$N_2$=5:1:4(vol./vol./vol.; $CH_4$ concentration is 50%) as feed gas. The catalyst of COMPARATIVE EXAMPLE 3 was also evaluated at 750° C. when other conditions remain unchanged.

Table 1 shows the reaction results of oxidative coupling of methane catalyzed by the catalysts of the EXAMPLES and COMPARATIVE EXAMPLES.

TABLE 1

| Catalyst | Temp. (° C.) | Conversion (%) | Selectivity (%) | | | $C_2$-$C_3$ yield (%) | ethylene/ethane (mol/mol) |
|---|---|---|---|---|---|---|---|
| | | | $C_2$ | $C_3$ | $C_2$-$C_3$ | | |
| Example 1 | 620 | 14.8 | 45.7 | 4.8 | 50.5 | 7.5 | 1.45 |
| | 640 | 22.0 | 57.1 | 5.8 | 62.9 | 13.8 | 1.66 |
| | 650 | 24.3 | 62.6 | 5.0 | 67.6 | 16.4 | 1.65 |
| | 680 | 25.5 | 68.2 | 5.6 | 73.8 | 18.8 | 1.74 |
| | 700 | 26.7 | 70.7 | 5.8 | 76.5 | 20.4 | 1.78 |
| Example 2 | 620 | 12.5 | 46.3 | 3.9 | 50.2 | 6.3 | 1.47 |
| | 650 | 21.7 | 62.1 | 5.2 | 67.3 | 14.6 | 1.62 |
| | 700 | 26.4 | 68.5 | 6.8 | 75.3 | 19.9 | 1.77 |
| Example 3 | 620 | 13.3 | 43.7 | 4.6 | 48.3 | 6.4 | 1.46 |
| | 650 | 22.8 | 59.8 | 5.3 | 65.1 | 14.8 | 1.62 |
| | 700 | 25.9 | 69.1 | 5.8 | 74.9 | 19.4 | 1.72 |
| Example 4 | 620 | 14.2 | 44.6 | 4.1 | 48.7 | 6.9 | 1.44 |
| | 650 | 23.5 | 61.4 | 4.8 | 66.2 | 15.6 | 1.67 |
| | 700 | 25.8 | 70.0 | 5.8 | 75.8 | 19.6 | 1.72 |
| Example 5 | 620 | 14.6 | 44.0 | 5.2 | 49.2 | 7.2 | 1.45 |
| | 650 | 23.7 | 60.6 | 6.4 | 67.0 | 15.9 | 1.63 |
| | 700 | 25.8 | 68.9 | 6.8 | 75.7 | 19.5 | 1.76 |
| Example 6 | 620 | 13.8 | 44.2 | 4.7 | 48.9 | 6.7 | 1.39 |
| | 650 | 22.6 | 60.3 | 5.4 | 65.7 | 14.8 | 1.43 |
| | 700 | 24.9 | 69.7 | 5.9 | 75.6 | 18.8 | 1.68 |
| Example 7 | 620 | 14.2 | 44.7 | 4.6 | 49.3 | 7.0 | 1.42 |
| | 650 | 23.5 | 59.8 | 6.0 | 65.8 | 15.5 | 1.60 |
| | 700 | 25.8 | 69.5 | 6.5 | 76.0 | 19.6 | 1.75 |
| Example 8 | 620 | 13.7 | 44.2 | 4.7 | 48.9 | 6.7 | 1.40 |
| | 650 | 24.0 | 59.9 | 5.9 | 65.8 | 15.8 | 1.56 |
| | 700 | 25.5 | 68.9 | 6.4 | 75.3 | 19.2 | 1.75 |
| Example 9 | 620 | 14.5 | 44.3 | 4.6 | 48.9 | 7.1 | 1.45 |
| | 650 | 23.7 | 60.4 | 5.8 | 66.2 | 15.7 | 1.60 |
| | 700 | 26.0 | 69.9 | 6.1 | 76.0 | 19.8 | 1.73 |
| Example 10 | 620 | 15.0 | 44.3 | 4.9 | 49.2 | 7.4 | 1.43 |
| | 650 | 24.2 | 61.0 | 5.5 | 66.5 | 16.1 | 1.57 |
| | 700 | 25.9 | 69.9 | 5.8 | 75.7 | 19.6 | 1.73 |
| Example 11 | 620 | 11.3 | 44.8 | 3.1 | 47.9 | 5.4 | 1.35 |
| | 650 | 19.9 | 63.2 | 4.2 | 67.4 | 13.4 | 1.46 |
| | 700 | 22.5 | 68.7 | 5.5 | 74.2 | 16.7 | 1.63 |
| Example 12 | 620 | 13.5 | 45.2 | 4.6 | 49.8 | 6.7 | 1.40 |
| | 650 | 19.3 | 58.4 | 5.7 | 64.1 | 12.4 | 1.68 |
| | 700 | 23.7 | 67.9 | 6.2 | 74.1 | 17.6 | 1.72 |
| Example 13 | 620 | 12.7 | 44.7 | 3.8 | 48.5 | 6.2 | 1.38 |
| | 650 | 20.4 | 57.5 | 5.3 | 62.8 | 12.8 | 1.59 |
| | 700 | 21.9 | 65.2 | 6.6 | 71.8 | 15.7 | 1.66 |
| Example 14 | 620 | 14.2 | 45.1 | 4.4 | 48.6 | 6.4 | 1.39 |
| | 650 | 21.4 | 60.5 | 5.0 | 63.5 | 12.5 | 1.67 |
| | 700 | 23.8 | 68.8 | 5.4 | 72.3 | 18.8 | 1.70 |
| Comparative example 1 | 620 | 0 | 0 | 0 | 0 | 0 | 0 |
| | 650 | 2.6 | 0 | 0 | 0 | 0 | 0 |
| | 700 | 3.5 | 0 | 0 | 0 | 0 | 0 |
| Comparative example 2 | 620 | 0 | 0 | 0 | 0 | 0 | 0 |
| | 650 | 3.5 | 0 | 0 | 0 | 0 | 0 |
| | 700 | 4.7 | 0 | 0 | 0 | 0 | 0 |
| Comparative example 3 | 650 | 3.6 | 0 | 0 | 0 | 0 | 0 |
| | 680 | 7.8 | 15.3 | 3.0 | 18.3 | 1.4 | 1.18 |
| | 700 | 20.7 | 56.2 | 5.9 | 62.1 | 12.8 | 1.66 |
| | 750 | 23.2 | 61.9 | 6.8 | 68.7 | 15.9 | 1.93 |

As shown in Table 1, the catalysts provided by the present disclosure or the catalysts obtained by the preparation method provided by the present disclosure, achieve unprecedented low-temperature activity and selectivity for oxidative coupling of methane, due to the presence of the manganese composite oxide having a perovskite structure and/or a spinel structure in the active components. Such catalysts are capable of converting 27% methane with a high $C_2$-$C_3$ hydrocarbon selectivity of 76% even at low reaction temperature of 620-700° C. and normal pressure. More specially, in the comparative examples, the catalysts become almost inactive below 700° C. and it is even more impossible to talk about selectivity. Compared with the prior art, thus, the present disclosure has also made remarkable progress and unexpected effect.

Figure 4:
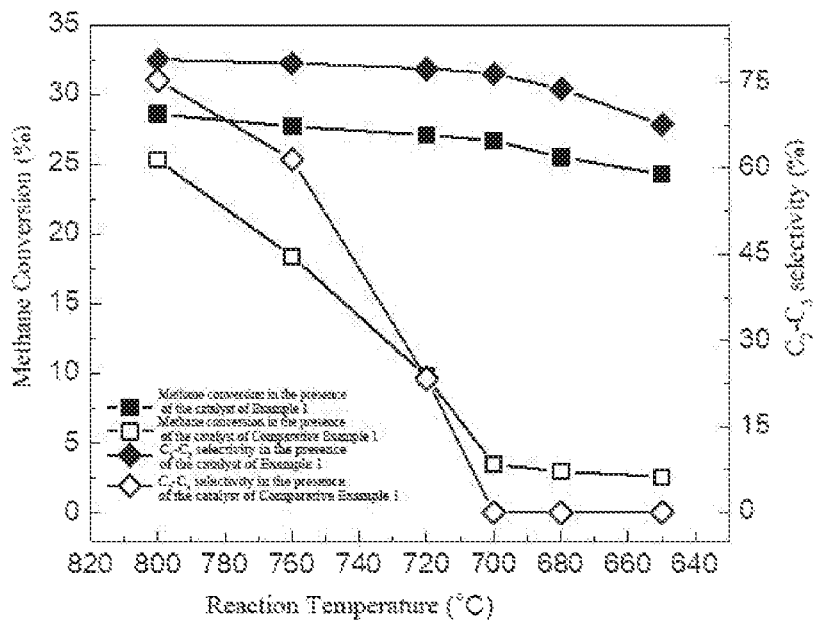
FIG. 4 is a graph showing temperature-dependent methane conversion and $C_2$-$C_3$ selectivity for oxidative coupling of methane respectively catalyzed by $3Mn_2O_3$-$10Na_2WO_4$-$10MnTiO_3$-$77SiO_2$ catalyst as prepared in Example 1 and $3Mn_2O_3$-$10Na_2WO_4$-$87SiO_2$ catalyst as prepared in Comparative Example 1.
Figure 5:
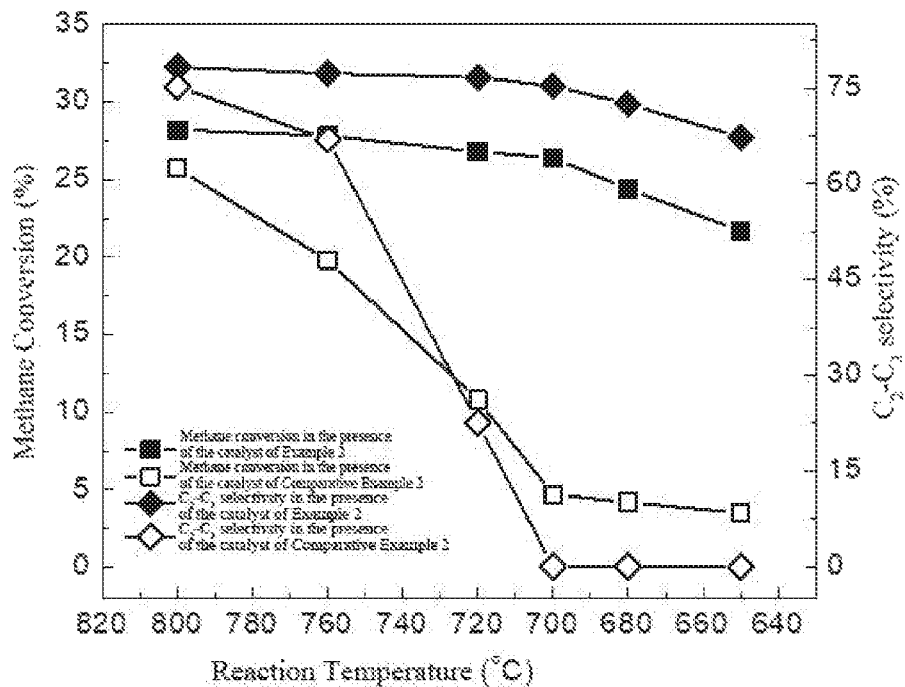
FIG. 5 is a graph showing temperature-dependent methane conversion and $C_2$-$C_3$ selectivity for oxidative coupling of methane respectively catalyzed by $5Mn_2O_3$-$5Na_2WO_4$-$8MnTiO_3$-$82SiO_2$ catalyst as prepared in Example 2 and $3Mn_2O_3$-$10Na_2WO_4$-87Sillicalite-1 catalyst as prepared in Comparative Example 2.

FIG. 4 is a graph showing temperature-dependent methane conversion and $C_2$-$C_3$ selectivity for oxidative coupling of methane respectively catalyzed by $3Mn_2O_3$-$10Na_2WO_4$-$10MnTiO_3$-$77SiO_2$ catalyst as prepared in Example 1 and $3Mn_2O_3$-$10Na_2WO_4$-$87SiO_2$ catalyst as prepared in Comparative Example 1; FIG. 5 is a graph showing temperature-dependent methane conversion and $C_2$-$C_3$ selectivity for oxidative coupling of methane respectively catalyzed by $5Mn_2O_3$-$5Na_2WO_4$-$8MnTiO_3$-$82SiO_2$ catalyst as prepared in Example 2 and $3Mn_2O_3$-$10Na_2WO_4$-$87$Sillicalite-1 catalyst as prepared in Comparative Example 2. As shown in FIG. 4 and FIG. 5, compared with the conventional catalysts, the catalysts provided by the present disclosure or the catalysts obtained by the preparation method provided by the present disclosure, achieve promising low-temperature activity and selectivity for oxidative coupling of methane, thus, the present disclosure has made remarkable progress compared with the prior art.

Application Example 2

The catalyst reaction evaluation and product analysis system are the same as in Application Example 1.

Figure 6:
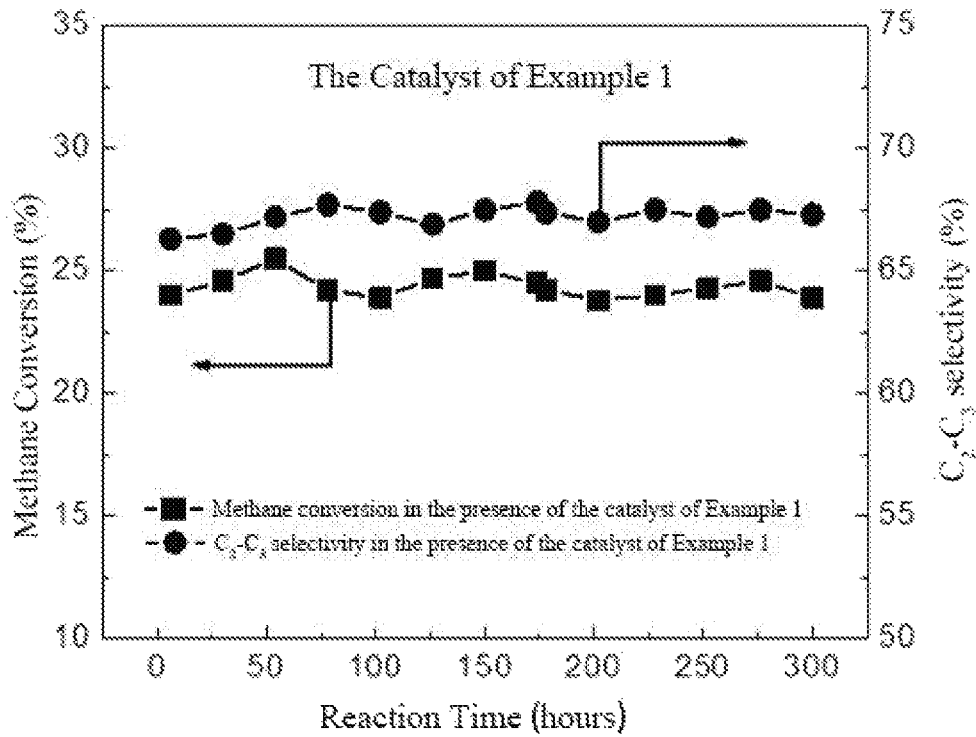
FIG. 6 is a graph showing the results of the stability test of the $3Mn_2O_3$-$10Na_2WO_4$-$10MnTiO_3$-$77SiO_2$ catalyst as prepared in Comparative Example 1 at 650° C. for 300 hours in oxidative coupling of methane.

The purpose of this application example is to investigate the stability of the catalysts obtained the examples in the oxidative coupling reaction of methane. The catalyst stability test of 300 hours was carried out under atmospheric pressure at 650° C. and a gas hourly space velocity (GHSV) of 8000 mL·h$^{-1}$·g$^{-1}$ (calculated by methane and oxygen) for a gaseous mixture of $CH_4$:$O_2$:$N_2$=5:1:4(vol./vol./vol.); $CH_4$ concentration is 50%) as feed gas, using 0.8 grams $3Mn_2O_3$-$10Na_2WO_4$-$10MnTiO_3$-$77SiO_2$ catalyst of EXAMPLE 1, with the results shown in FIG. 6. As indicated in FIG. 6, the catalyst of the invention has good reaction stability, achieving excellent reactivity maintenance with methane conversion around 24% and $C_2$-$C_3$ selectivity around 67% throughout entire 300 hours test.

Finally, it should be pointed out that: the above are only some of the preferred embodiments of the present invention and should not be construed as limiting the scope of protection of the present invention, Some non-essential improvements and adjustments made by those skilled in the art according to the above contents of the present invention all belong to the protection scope of the invention.

The invention claimed is:

1. A catalyst for oxidative coupling of methane consisting of three active components of manganese sesquioxide, sodium tungstate, manganese titanate, and a carrier of silica,
wherein the catalyst has a composition represented by the following formula: $xMn_2O_3$-$yNa_2WO_4$-$zMnTiO_3$-$(100$-$x$-$y$-$z)SiO_2$,
wherein x, y and z respectively representing the weight fraction occupied by manganese sesquioxide, sodium tungstate, manganese titanate in the catalyst, and wherein $0<x\leq20$, $1\leq y\leq20$, $1\leq z\leq40$.

2. The catalyst of claim 1, wherein $1.5\leq x\leq18$, $4\leq y\leq18$, and $2\leq z\leq35$.

3. A catalyst, comprising a manganese sesquioxide, a tungstate, a manganese composite oxide having a perovskite structure and/or a spinel structure, and a carrier,
wherein the manganese sesquioxide, the tungstate, the manganese composite oxide having a perovskite structure and/or a spinel structure are supported on the carrier,
or
the manganese sesquioxide and the tungstate are supported on an admixture of the said manganese composite oxide having a perovskite structure and/or a spinel structure and the said carrier,
wherein, based on 100 parts by weight of the catalyst, the content of the manganese sesquioxide is a parts by weight, the content of the tungstate is b parts by weight, the content of the manganese composite oxide having the perovskite structure and/or the spinel structure is c parts by weight, and the content of the carrier is d parts by weight, and wherein $0<a\leq20$, $1\leq b\leq20$, $1\leq c\leq40$, $20\leq d\leq98$.

4. The catalyst of claim 3, wherein the catalyst is consisted of a manganese sesquioxide, a tungstate, a manganese composite oxide having a perovskite structure and/or a spinel structure, and a carrier,
wherein based on 100 parts by weight of the catalyst, the content of the manganese sesquioxide is ranged from >0 parts by weight to ≤20 parts by weight,
the content of the tungstate is ranged from 1.0 parts by weight to 20 parts by weight,
the content of the manganese composite oxide having a perovskite structure and/or a spinel structure is ranged from 1 part by weight to 40 parts by weight,
the balance is the carrier.

5. The catalyst of claim 3, wherein the manganese composite oxide having the perovskite structure and/or the spinel structure comprises at least one element selected from Ti, Fe, Co, Ni, Li, Pb, Cd, Sn, In, Ge, Ga, Sb, Bi, Te, Se, Zr, Hf, V, Nb, Ta, Cr, Mo, W, Ba, Mg, Ce, La, Pr, Nd, Sm, Ca, Sr, K or combinations thereof.

6. The catalyst of claim 3, wherein the manganese composite oxide having a perovskite structure and/or a spinel structure is at least one selected from manganese titanate, manganese ferrite, manganese cobaltate, manganese nickelate, lithium manganite, lithium nickel cobalt manganese oxide, manganese plumbite, cadmium acid manganese, manganese stannate, manganese germanate, manganese gallate, bismuth manganate, manganese tellurite, manganese selenate, vanadium manganate, manganese niobate, manganese tantalite, manganese chromate, barium manganate, magnesium manganate, $LnAFeMnO_6$(Ln=La, Pr, Nd, Sm, Ce; A=Ca, Sr, Ba), $La_{0.5}Sr_{0.5}Mn_{1-m}Fe_mO_3$, $Ca_\alpha La_\beta K_{1-\alpha-\beta}Mn_{0.5}Fe_{0.5}O_3$, $Ca_p La_q K_{1-p-q}Mn_{0.78}Fe_{0.22}O_3$, $Bi_{0.5}Ca_{0.5-n}La_n Fe_{0.3}Mn_{0.7}O_3$ or combinations thereof; $0<m\leq0.25$, $0<\alpha\leq0.25$, $0<\beta\leq0.25$, $0<p\leq0.25$, $0<q\leq0.25$, $0<n\leq0.25$
the manganese composite oxide having a perovskite structure and/or a spinel structure comprises particles having a size varied from 100 to 2000 mesh.

7. The catalyst of claim 3, wherein the carrier is selected from SiC, $Fe_2O_3$, $Fe_3O_4$, $TiO_2$, $ZrO_2$, $Al_2O_3$, $La_2O_3$, CaO, SrO, MgO, $SiO_2$ or combinations thereof,
the carrier having a particle size varied from 100 to 2000 mesh,
wherein the carrier having a specific surface varied from 10 to 1000 m$^2$/g,
wherein the carrier having a pore volume varied from 0.1 to 1.2 mL/g,
wherein the carrier having a most probable pore size varied from 2.0 to 20.0 nm.

8. The catalyst of claim 7, wherein the carrier is $SiO_2$,
wherein the carrier having a particle size varied from 100 to 1000 mesh,
wherein the carrier having a specific surface varied from 50 to 250 m$^2$/g,
wherein the carrier having a pore volume varied from 0.5 to 0.9 mL/g, wherein the carrier having a most probable pore size varied from 2.0 to 10.0 nm.

9. A method for oxidative coupling of methane, comprising: bringing the catalyst of claim 3 into contact with a feed gas stream containing methane and oxygen to have the methane reacting with oxygen under oxidative coupling of methane conditions.

10. The method of claim 9, wherein the methane to oxygen volume ratio in the feed gas stream is 3:1~8:1; the reaction temperature is from 620 to 900° C., the reaction pressure is from 0.1 to 2 MPa, on the basis of the total amount of methane and oxygen, the gas hourly space velocity is from 3000-50000 mL·h$^{-1}$·g$^{-1}$.

* * * * *